(12) United States Patent
Hayward

(10) Patent No.: US 6,245,745 B1
(45) Date of Patent: Jun. 12, 2001

(54) HYGROMYCIN A DERIVATIVES

(75) Inventor: Mathew Merrill Hayward, Old Lyme, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/453,429

(22) Filed: Dec. 2, 1999

Related U.S. Application Data

(60) Provisional application No. 60/110,618, filed on Dec. 2, 1998.

(51) Int. Cl.[7] .................... A61K 31/70; C07H 15/00
(52) U.S. Cl. .................... 514/25; 514/23; 536/16.8; 536/17.9; 536/18.1
(58) Field of Search .................... 536/16.8, 18.1, 536/17.9; 574/25, 23

(56) References Cited

FOREIGN PATENT DOCUMENTS

| | | |
|---|---|---|
| WO 9957125A | 11/1999 | (EP) . |
| WO 9957127A | 11/1999 | (EP) . |

OTHER PUBLICATIONS

S. Hayashi et al.: "Structure–activity Relationships of Hygromycin A and Its Analogs: Protein Synthesis Inhibition Activity in a Cell Free System"; *J. Antibiotics*, vol. 50, No. 6, 1997, pp. 514–521, XP002120210, figure 1.

*Primary Examiner*—Elli Peselev
(74) *Attorney, Agent, or Firm*—Peter C. Richardson; Paul H. Ginsburg; Israel Nissenbaum

(57) ABSTRACT

This invention relates to compounds of the formula

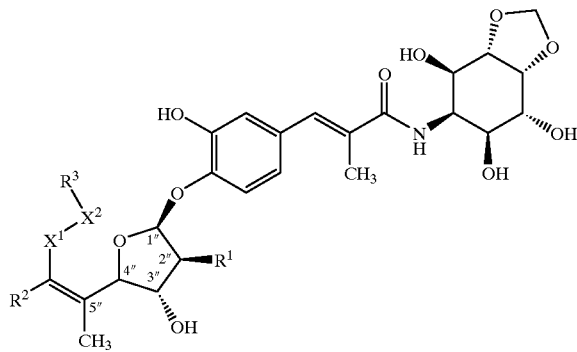

and to pharmaceutically acceptable salts and solvates thereof, wherein $R^1$, $R^2$, $R^3$, $X^1$ and $X^2$ are as defined herein. The compounds of formula 1 are antibacterial and antiprotozoal agents that may be used to treat various bacterial and protozoal infections and disorders related to such infections. The invention also relates to pharmaceutical compositions containing the compounds of formula 1, methods of treating bacterial and protozoal infections by administering the compounds of formula 1, and methods of preparing certain compounds of formula 1.

16 Claims, No Drawings

HYGROMYCIN A DERIVATIVES

This application claim benefit to provisional application 60/110,618 Dec. 2, 1998.

BACKGROUND OF THE INVENTION

This invention relates to novel hygromycin A derivatives that are useful as antibacterial and antiprotozoal agents in mammals, including man, as well as in fish and birds. This invention also relates to pharmaceutical compositions containing the novel compounds and to methods of treating bacterial and protozoal infections in mammals, fish and birds by administering the novel compounds to mammals, fish and birds requiring such treatment.

Hygromycin A is a fermentation-derived natural product first isolated from *Streptomyces hygroscopicus* in 1953. As an antibiotic, hygromycin A possesses activity against human pathogens and is reported to possess potent in vitro activity against *Serpulina (Treponema) hyodysenteriae* which causes swine dysentery. Several references refer to semisynthetic modifications of hygromycin A, including the following: derivatization of the 5" ketone of hygromycin A to the 2,4-dinitrophenylhydrazone is referred to in K. Isono et al., *J. Antibiotics* 1957, 10, 21, and R. L. Mann and D. O. Woolf, *J. Amer Chem. Soc.* 1957, 79, 120. K. Isono et al., ibid., also refer to the thiosemicarbazone at 5"; reduction of the 5" ketone of hygromycin A to the 5" alcohol is referred to in R. L. Mann and D. O. Woolf, ibid., as well as in S. J. Hecker et al., *Bioorg. Med. Chem. Lett.* 1992, 2, 533 and S. J. Hecker et al., *Bioorg. Med. Chem. Lett.* 1993, 3, 295; furanose analogues are referred to in B. H. Jaynes et al., *Bioorg. Med. Chem. Lett.* 1993, 3, 1531, and B. H. Jaynes et al., *J. Antibiot.* 1992, 45, 1705; aromatic ring analogues are referred to in S. J. Hecker et al., *Bioorg. Med. Chem. Lett.* 1993, 3, 289, and C. B. Cooper et al., *Bioorg. Med. Chem. Lett.* 1997, 7, 1747; enamide analogues are referred to in S. J. Hecker et al., *Bioorg. Med. Chem. Lett.* 1992, 2, 533; aminocyclitol analogues are referred to in S. J. Hecker et al., *Bioorg. Med. Chem. Lett.* 1992, 2, 1015, and in S. J. Hecker et al., *Bioorg. Med. Chem. Lett.* 1992, 2, 1043. The hygromycin A derivatives of the present invention possess broad activity against both gram-negative and gram-positive bacteria and protozoa. Hygromycin A derivatives are also described and claimed in U.S. provisional patent application Nos. 60/084,042 (filed May 4, 1998) and 60/084,058 (filed May 4, 1998), both of which U.S. provisional applications are incorporated herein by reference in their entirety.

SUMMARY OF THE INVENTION

The present invention relates to compounds of the formula

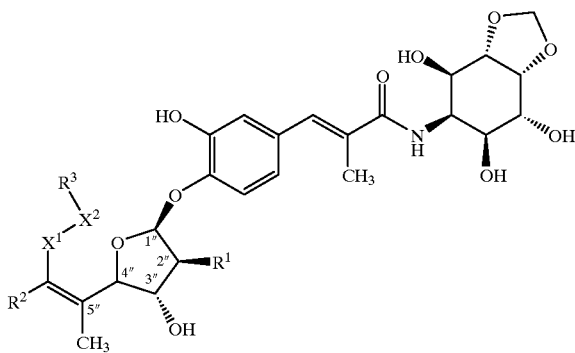

1 and to pharmaceutically acceptable salts and solvates thereof wherein:

each $X^1$ is selected from —$CR^6R^7$—, —$S(O)_n$— wherein n is 0 to 2, —$NR^6$— and a bond and $X^2$ is selected from —$CR^6R^7$—, —$S(O)_n$— wherein n is 0 to 2, —$NR^6$—, O, and a bond, except that (a) if either $X^1$ or $X^2$ is S, or S(O) then the other moiety ($X^1$ or $X^2$) is —$CR^6R^7$— or a bond; (b) if either $X^1$ or $X^2$ is $SO_2$ then the other moiety ($X^1$ or $X^2$) is —$NR^6$—, —$CR^6R^7$— or a bond; (c) if $X^1$ is —$NR^6$—, then $X^2$ is selected from $SO_2$ and —C(O)—; and (d) if $X^2$ is O than $X^1$ must be —$CR^6R^7$—;

$R^1$ is H or OH;

$R^2$ is H, $C_1$–$C_6$ alkyl, or halo, wherein the foregoing $R^2$ alkyl group is optionally substituted by 1 or 2 $R^4$ groups;

or where $X^2$ is —$NR^6$—, then $R^3$ and $X^2$ may be taken together to form a 5 to 12 membered ring, wherein said ring is saturated or partially unsaturated with up to 3 carbon-carbon double bonds, the carbon atoms of said ring are optionally subsituted by 1 to 3 $R^4$ groups, and the ring optionally contains up to 2 additional hetero moieties (in addition to the $X^2$ moiety which is —$NR^6$—) selected from O, $S(O)_j$ wherein j is an integer from 0 to 2, and —$NR^6$—, with the proviso that two O atoms, two S atoms, an O and S atom, an N and O atom, and an N and S atom are not attached directly to each other;

each $R^3$ is independently selected from H, $C_1$–$C_{10}$ alkyl, —$(CR^6R^7)_t(C_6$–$C_{10}$ aryl), —$(CR^6R^7)_t$(4–10 membered heterocyclic), —$C(O)(CR^6R^7)_t(C_6$–$C_{10}$ aryl), —$C(O)(CR^6R^7)_t$(4–10 membered heterocyclic), —$C(O)NR^6(CR^6R^7)_t(C_6$–$C_{10}$ aryl), and —$C(O)NR^6(CR^6R^7)_t$(4–10 membered heterocyclic), wherein t is an integer ranging from 0 to 5, said alkyl group optionally contains 1 or 2 hetero moieties selected from O, —$S(O)_j$— wherein j is an integer ranging from 0 to 2, and —$NR^6$— with the proviso that two O atoms, two S atoms, an O and S atom, an N and O atom, and an N and S atom are not attached directly to each other; the —$(CR^6R^7)_t$— moieties of the foregoing $R^3$ groups optionally include a carbon-carbon double or triple bond where t is an integer between 2 and 5; and the heterocyclic and aryl moieties of the foregoing $R^3$ groups are optionally substituted by 1 to 5 $R^4$ groups;

each $R^4$ is independently selected from $C_1$–$C_{10}$ alkyl, $C_2$–$C_{10}$ alkenyl, $C_2$–$C_{10}$ alkynyl, halo, cyano, nitro, trifluoromethyl, trifluoromethoxy, azido, hydroxy, $C_1$–$C_6$ alkoxy, —C(O)$R^5$, —C(O)O$R^5$, —N$R^6$C(O)O$R^8$, —OC(O)$R^5$, —N$R^6$SO$_2R^8$, —SO$_2$N$R^5R^6$, —N$R^6$C(O)$R^5$, —C(O)N$R^5R^6$, —N$R^5R^6$, —S(O)$_j$(C$R^6R^7$)$_m$(C$_6$–C$_{10}$ aryl), —S(O)$_j$(C$_1$–C$_6$ alkyl), —(C$R^6R^7$)$_m$(C$_6$–C$_{10}$ aryl), —O(C$R^6R^7$)$_m$(C$_6$–C$_{10}$ aryl), —N$R^6$(C$R^6R^7$)$_m$(C$_6$–C$_{10}$ aryl), —(C$R^6R^7$)$_m$(4–10 membered heterocyclic), —C(O)(C$R^6R^7$)$_m$(C$_6$–C$_{10}$ aryl), and —C(O)(C$R^6R^7$)$_m$(4–10 membered heterocyclic), wherein m is an integer from 0 to 4; j is an integer from 0 to 2, and said alkyl, alkenyl, alkynyl, aryl and heterocyclic moieties of the foregoing $R^4$ groups are optionally substituted by 1 to 3 substituents independently selected from halo, cyano, nitro, trifluoromethyl, trifluoromethoxy, azido, —N$R^6$SO$_2R^8$, —SO$_2$N$R^5R^6$, —C(O)$R^5$, —C(O)O$R^5$, —OC(O)$R^5$, —N$R^6$C(O)O$R^8$, —N$R^6$C(O)$R^5$, —C(O)N$R^5R^6$, —N$R^5R^6$, —O$R^5$, $C_1$–$C_{10}$ alkyl, —(C$R^6R^7$)$_m$(C$_6$–C$_{10}$ aryl), and —(C$R^6R^7$)$_m$(4–10 membered heterocyclic), wherein m is an integer from 0 to 4;

each $R^5$ is independently selected from H, $C_1$–$C_{10}$ alkyl, —(C$R^6R^7$)$_m$(C$_6$–C$_{10}$ aryl), and —(C$R^6R^7$)$_m$(4–10 membered heterocyclic), wherein m is an integer from 0 to 4, and the foregoing $R^5$ substituents, except H, are optionally substituted by 1 to 3 substituents independently selected from halo, cyano, nitro, trifluoromethyl, trifluoromethoxy, azido, —C(O)$R^6$, —C(O)O$R^6$, —OC(O)$R^6$, —N$R^6$C(O)$R^7$, —C(O)N$R^6R^7$, —N$R^6R^7$, hydroxy, $C_1$–$C_6$ alkyl, and $C_1$–$C_6$ alkoxy;

each $R^6$ and $R^7$ is independently H, —C(O)(C$_1$–C$_6$ alkyl), $C_1$–$C_6$ alkyl or fluoro; and, $R^8$ is selected from the substituents provided in the definition of $R^5$ except $R^8$ is not H.

Specific embodiments of said compounds of formula 1 include those wherein $X^1$ is —CH$_2$— and $X^2$ is O.

Other specific embodiments of said compounds of formula 1 include those wherein $X^1$ is —CH$_2$—, $X^2$ is O, and $R^3$ is —(C$R^6R^7$)$_t$(C$_6$–C$_{10}$ aryl) wherein t is as defined above, $R^6$ and $R^7$ are both H, and said aryl group is optionally substituted by 1 to 4 $R^4$ groups. In a more specific embodiment, said aryl group is a phenyl group optionally substituted by 1 to 4 $R^4$ groups.

Other specific embodiments of said compounds of formula 1 include those wherein $X^1$ is —CH$_2$—, $X^2$ is O, and $R^3$ is —(C$R^6R^7$)$_t$(4–10 membered heterocyclic), wherein t is as defined above, $R^6$ and $R^7$ are both H, and said heterocyclic group is optionally substituted by 1 to 4 $R^4$ groups. In a more specific embodiment, said heterocyclic group is a pyridyl group or benzothiazolyl group optionally substituted by 1 to 4 $R^4$ groups.

Other specific embodiments of said compounds of formula 1 include those wherein $X^1$ is —CH$_2$—, $X^2$ is O, and $R^3$ is —C(O)(C$R^6R^7$)$_t$(C$_6$–C$_{10}$ aryl) wherein t is as defined above, $R^6$ and $R^7$ are both H, and said aryl group is optionally substituted by 1 to 4 $R^4$ groups. In a more specific embodiment, said aryl group is a phenyl group optionally substituted by 1 to 4 $R^4$ groups.

Other specific embodiments of said compounds of formula 1 include those wherein $X^1$ is —CH$_2$—, $X^2$ is O, and $R^3$ is —C(O)N$R^6$(C$R^6R^7$)$_t$(C$_6$–C$_{10}$ aryl) wherein t is as defined above, $R^6$ and $R^7$ are both H, and said aryl group is optionally substituted by 1 to 4 $R^4$ groups. In a more specific embodiment, said aryl group is a phenyl group optionally substituted by 1 to 4 $R^4$ groups.

Specific preferred compounds of formula 1 include those selected from the group consisting of:

3-(4-((2S,3S,4S,5R)-3,4-Dihydroxy-5-(3-hydroxy-1-methyl-(1E)-propenyl)-tetrahydro-furan-2-yloxy)-3-hydroxy-phenyl)-2-methyl-N-((3aS,4R,5R,6S,7R,7aR)-4,6,7-trihydroxy-benzo(1,3)dioxol-5-yl)-(2E)-acrylamide;

3-(4-((2S,3S,4S,5R)5-(3-Benzyloxy-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-benzo(1,3)dioxol-5-yl)-(2E)-acrylamide;

3-(4-((2S,3S,4S,5R)5-(3-(3-Chloro-benzyloxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-benzo(1,3)dioxol-5-yl)-(2E)-acrylamide;

3-(4-((2S,3S,4S,5R)5-(3-(Biphenyl-2-ylmethoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-benzo(1,3)dioxol-5-yl)-(2E)-acrylamide;

3-(4-((2S,3S,4S,5R)5-(3-(4-tert-Butyl-benzyloxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-benzo(1,3)dioxol-5-yl)-(2E)-acrylamide;

3-(4-((2S,3S,4S,5R)5-(3-(4-Fluoro-benzyloxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-benzo(1,3)dioxol-5-yl)-(2E)-acrylamide;

Benzoic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

4-Methoxy-benzoic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

2-Fluoro-benzoic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

3-Chloro-benzoic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

4-Trifluoromethyl-benzoic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

Benzyl-carbamic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

Phenyl-carbamic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

3-(4-((2S,3S,4S,5R)-5-(3-(3-Chloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3-Fluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3,5-Difluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Fluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Chloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-4-fluro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Chloro-3-fluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3,5-Dichloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3-chloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(pyridin-3-yloxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3-chloro-4-fluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3-Methoxy-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,4-Dichloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,4-Difluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-chloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,6-Difluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3-chloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5yl)-(2E)-acrylamide;

3-(4-((2S,3S,4S,5R)-5-(3-(2-Fluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Fluoro-2-propyl-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-phenoxy-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Benzyl-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Benzoyl-4-chloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Cyano-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(Indan-4-yloxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Chloro-2-fluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,6-Dichloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-4-fluoro-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-5-fluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,3,4-Trichloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,3-Dichloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,5-Dichloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,5-Dichloro-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Fluoro-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,4-Dichloro-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-5-fluoro-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-3,5-difluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-3,5-difluoro-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,4,5-Trichloro-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,4,5-Trichloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Fluoro-2-trifluoromethyl-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Fluoro-2-trifluoromethyl-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Trifluoromethyl-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Trifluoromethyl-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-4-fluoro-phenoxy)-1,2-dimethyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-phenoxy)-1,2-dimethyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2-Chloro-4-fluoro-phenoxy)-1-methyl-(1Z)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2-Chloro-4-fluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R, 7aR)-4,6,7-trihydroxy-hexahydro-benzo(1,3)dioxol-5-yl)-(2E)-acrylamide;

3-(4-((2S,4S,5R)-5-(3-(2,3-Dichloro-4-fluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,3,4-trichloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,4,5-trichloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,5-Dichloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(3-Chloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(3-Fluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,4-Difluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2-Chloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,4-Dichloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2-Chloro-5-fluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2-Chloro-3,5-difluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(3,5-Difluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(3-Fluoro-4-chloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2-Fluoro-4-chloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide; and the pharmaceutically acceptable salts of the foregoing compounds.

Other specific embodiments of the present invention include the following compounds:

3-(4-{(2S,3S,4S,5R)-5-[3-(Benzothiazol-6-yloxy)-1-methyl-(1E)-propenyl]-3,4-dihydroxy-tetrahydro-furan-2-yloxy}-3-hydroxy-phenyl)-2-methyl-N- ((3aS,4R,5R,6S,7R,7aR)-4,6,7-trihydroxy-hexahydro-benzo[1,3]dioxol-5-yl)-acrylamide;

3-(4-{(2S,3S,4S,5R)-5-[3-(Benzothiazol-6-yloxy)-1-methyl-(1Z)-propenyl]-3,4-dihydroxy-tetrahydro-furan-2-yloxy}-3-hydroxy-phenyl)-2-methyl-N- ((3aS,4R,5R,6S,7R,7aR)-4,6,7-trihydroxy-hexahydro-benzo[1,3]dioxol-5-yl)-acrylamide;

3-(4-{(2S,3S,4S,5R)-5-[3-(2-Chloro-pyridin-3-yloxy)-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-acrylamide;

3-(4-{(2S,3S,4S,5R)-5-[3-(2-Chloro-pyridin-3-yloxy)-1-methyl-(1Z)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-acrylamide;

3-[4-((2S,3S,4S,5R)-5-{3-[2,4-Dichloro-6-(methoxyimino-methyl)-phenoxy]-1-methyl-(1E)-propenyl}-3,4-dihydroxy-tetrahydro-furan-2-yloxy)-3-hydroxy-phenyl]-2-methyl-N-((3aS,4R,5R,6S,7R,7aR)-4,6,7-trihydroxy-hexahydro-benzo[1,3]dioxol-5-yl)-(2E)-acrylamide;

3-[4-((2S,3S,4S,5R)-5-{3-[2,4-Dichloro-6-(methoxyimino-methyl)-phenoxy]-1-methyl-(1Z)-propenyl}-3,4-dihydroxy-tetrahydro-furan-2-yloxy)-3-hydroxy-phenyl]-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-(2-Acetyl-4,6-dichloro-phenoxy)-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydrobenzo[1,3]dioxol-5-yl)-(2E)-acrylamide;

3-(4-{(2S,3S,4S,5R)-5-[3-(2-Acetyl-4,6-dichloro-phenoxy)-1-methyl-(1Z)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-3,4-Dihydroxy-5-[3-(1H-indol-5-yloxy)-1-methyl-(1E)-propenyl]-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-3,4-Dihydroxy-5-[3-(1H-indol-5-yloxy)-1-methyl-(1Z)-propenyl]-tetrahydro-furan-2- yloxy}-3-hydroxy-phenyl)-2-methyl-N- ((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-(2-Benzooxazol-2-yl-phenoxy)-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-acrylamide;

3-(4-{(2S,3S,4S,5R)-5-[3-(2-Benzothiazol-2-yl-phenoxy)-1-methyl-(1Z)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-5-(3-Benzenesulfonyl-1-methyl-(1E)-propenyl)-3,4-dihydroxy-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-5-(3-Benzenesulfonyl-1-methyl-(1Z)-propenyl)-3,4-dihydroxy-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-3-phenylsulfanyl-(1E)-propenyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-3-phenylsulfanyl-(1Z)-propenyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-3-phenylamino-(1E)-propenyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-3-phenylamino-(1Z)-propenyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-5-(2-Benzylsulfanyl-1-methyl-(1E)-vinyl)-3,4-dihydroxy-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-5-(2-Benzylsulfanyl-1-methyl-(1Z)-vinyl)-3,4-dihydroxy-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-2-phenylmethanesulfonyl-(1E)-vinyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-2-phenylmethanesulfonyl-(1Z)-vinyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-2-phenylsulfamoyl-(1E)-vinyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-2-phenylsulfamoyl-(1Z)-vinyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-5-(2-Fluoro-1-methyl-3-phenoxy-(1E)-propenyl)-3,4-dihydroxy-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-5-(2-Fluoro-1-methyl-3-phenoxy-(1Z)-propenyl)-3,4-dihydroxy-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

and the pharmaceutically acceptable salts and solvates of said compounds.

The invention also relates to a pharmaceutical composition for the treatment of a disorder selected from a bacterial infection, a protozoal infection, and disorders related to bacterial infections or protozoal infections, in a mammal, fish, or bird which comprises a therapeutically effective amount of a compound of formula 1, or a pharmaceutically acceptable salt thereof, and a pharmaceutically acceptable carrier.

The invention also relates to a method of treating a disorder selected from a bacterial infection, a protozoal infection, and disorders related to bacterial infections or protozoal infections, in a mammal, fish, or bird which comprises administering to said mammal, fish or bird a therapeutically effective amount of a compound of formula 1 or a pharmaceutically acceptable salt thereof.

The present invention also relates to a method of preparing compounds of the formula

3 and to pharmaceutically acceptable salts and solvates thereof wherein:

$X^2$ is O or S;

$R^1$ is H or OH;

$R^2$ is H, $C_1$–$C_6$ alkyl, or halo, wherein the foregoing $R^2$ alkyl group is optionally substituted by 1 or 2 $R^4$ groups;

R³ is —(CR⁶R⁷)$_t$(C₆–C₁₀ aryl) wherein t is an integer from 0 to 5 and the aryl moiety of the foregoing R³ group is optionally substituted by 1 to 5 R⁴ groups;

each R⁴ is independently selected from C₁–C₁₀ alkyl, C₂–C₁₀ alkenyl, C₂–C₁₀ alkynyl, halo, cyano, nitro, trifluoromethyl, trifluoromethoxy, azido, hydroxy, C₁–C₆ alkoxy, —C(O)R⁵, —C(O)OR⁵, —NR⁶C(O)OR⁸, —OC(O)R⁵, —NR⁶SO₂R⁸, —SO₂NR⁵R⁶, —NR⁶C(O)R⁵, —C(O)NR⁵R⁶, —NR⁵R⁶, —S(O)$_j$(CR⁶R⁷)$_m$(C₆–C₁₀ aryl), —S(O)$_j$(C₁–C₆ alkyl), —(CR⁶R⁷)$_m$(C₆–C₁₀ aryl), —O(CR⁶R⁷)$_m$(C₆–C₁₀ aryl), —NR⁶(CR⁶R⁷)$_m$(C₆–C₁₀ aryl), —(CR⁶R⁷)$_m$(4–10 membered heterocyclic), —C(O)(CR⁶R⁷)$_m$(C₆–C₁₀ aryl), and —C(O)(CR⁶R⁷)$_m$(4–10 membered heterocyclic), wherein m is an integer from 0 to 4; j is an integer from 0 to 2, and said alkyl, alkenyl, alkynyl, aryl and heterocyclic moieties of the foregoing R⁴ groups are optionally substituted by 1 to 3 substituents independently selected from halo, cyano, nitro, trifluoromethyl, trifluoromethoxy, azido, —NR⁶SO₂R⁸, —SO₂NR⁵R⁶, —C(O)R⁵, —C(O)OR⁵, —OC(O)R⁵, —NR⁶C(O)OR⁸, —NR⁶C(O)R⁵, —C(O)NR⁵R⁶, —NR⁵R⁶, —OR⁵, C₁–C₁₀ alkyl, —(CR⁶R⁷)$_m$(C₆–C₁₀ aryl), and —(CR⁶R⁷)$_m$(4–10 membered heterocyclic), wherein m is an integer from 0 to 4;

each R⁵ is independently selected from H, C₁–C₁₀ alkyl, —(CR⁶R⁷)$_m$(C₆–C₁₀ aryl), and —(CR⁶R⁷)$_m$(4–10 membered heterocyclic), wherein m is an integer from 0 to 4, and the foregoing R⁵ substituents, except H, are optionally substituted by 1 to 3 substituents independently selected from halo, cyano, nitro, trifluoromethyl, trifluoromethoxy, azido, —C(O)R⁶, —C(O)OR⁶, —OC(O)R⁶, —NR⁶C(O)R⁷, —C(O)NR⁶R⁷, —NR⁶R⁷, hydroxy, C₁–C₆ alkyl, and C₁–C₆ alkoxy;

each R⁶ and R⁷ is independently H, —C(O)(C₁–C₆ alkyl), C₁–C₆ alkyl or fluoro; and, R⁸ is selected from the substituents provided in the definition of R⁵ except R⁸ is not H;

which comprises treating a compound of the formula

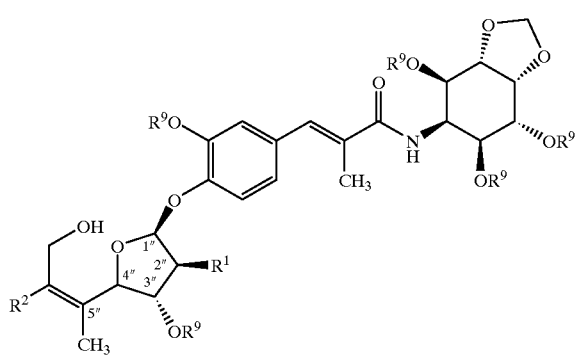

4 wherein R¹ and R² are as defined above, provided that if R¹ is hydroxy it is protected as —OR⁹, and R⁹ is a hydroxy protecting group, such as a silyl group, with a compound of the formula H—X²—(CR⁶R⁷)$_t$(C₆–C₁₀ aryl), wherein X², R⁶, R⁷ and t are as defined above, in the presence of triphenylphosphine and diethylazodicarboxylate, followed by deprotection of the R⁹-protected hydroxy groups.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

As used herein, unless otherwise indicated, the terms or phrases "bacterial infection(s)", "protozoal infection(s)", and "disorders related to bacterial infections or protozoal infections" include the following: pneumonia, otitis media, sinusitus, bronchitis, tonsillitis, and mastoiditis related to infection by *Streptococcus pneumoniae*, *Haemophilus influenzae*, *Moraxella catarrhalis*, *Staphylococcus aureus*, *Enterococcus faecalis*, *E. faecium*, *E. casselflavus*, *S. epidermidis*, *S. haemolyticus*, or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae*, *Legionella pneumophila*, *Streptococcus pneumoniae*, *Haemophilus influenzae*, or *Chlamydia pneumoniae*; blood and tissue infections, including endocarditis and osteomyelitis, caused by *S. aureus*, *S. haemolyticus*, *E. faecalis*, *E. faecium*, *E. durans*, including strains resistant to known antibacterials such as, but not limited to, beta-lactams, vancomycin, aminoglycosides, quinolones, chloramphenicol, tetracylines and macrolides; uncomplicated skin and soft tissue infections and abscesses, and puerperal fever related to infection by *Staphylococcus aureus*, coagulase-negative staphylococci (i.e., *S. epidermidis*, *S. hemolyticus*, etc.), *Streptococcus pyogenes*, *Streptococcus agalactiae*, Streptococcal groups C–F (minute-colony streptococci), viridans streptococci, *Corynebacterium minutissimum*, *Clostridium* spp., or *Bartonella henselae*; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis*, *Haemophilus ducreyi*, *Treponema pallidum*, *Ureaplasma urealyticum*, or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis*, *Neisseria gonorrhoeae*, *S. aureus*, *S. pneumoniae*, *S. pyogenes*, *H. influenzae*, or *Listeria* spp.; disseminated *Mycobacterium avium* complex (MAC) disease related to infection by *Mycobacterium avium*, or *Mycobacterium intracellulare*; infections caused by *Mycobacterium tuberculosis*, *M. leprae*, *M. paratuberculosis*, *M. kansasii*, or *M. chelonei*; gastroenteritis related to infection by *Campylobacter jejuni*, intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*. Bacterial infections and protozoal infections, and disorders related to such infections, which may be treated or prevented in animals include the following: bovine respiratory disease related to infection by *P. haemolytica, P. multocida, Mycoplasma bovis,* or Bordetella spp.; cow enteric disease related to infection by *E. coli* or protozoa (i.e., coccidia, cryptosporidia, etc.); dairy cow mastitis related to infection by *S. aureus, Strep. uberis, Streptococcus agalactiae, Streptococcus dysgalactiae,* Corynebacterium, or Enterococcus spp.; swine respiratory disease related to infection by *A. pleuro., P. multocida,* or Mycoplasma spp.; swine enteric disease related to infection by *E. coli, Lawsonia intracellularis,* Salmonella, or *Serpulina hyodysinteriae*; cow footrot related to infection by Fusobacterium spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*; skin and soft tissue infections in dogs and cats related to infection by *S. epidermidis, S. intermedius,* coagulase neg. Staphylococcus or *P. multocida*; and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoal infections, and disorders related to such infections, which may be treated or prevented in accord with the method of the present invention are referred to in J. P. Sanford et al., "The Sanford Guide To Antimicrobial Therapy," 26th Edition, (Antimicrobial Therapy, Inc., 1996).

The compounds of the present invention may be active against the bacteria and protoazoa, and associated conditions, referred to above, or specific strains of the bacteria and protozoa referred to above.

The term "halo", as used herein, unless otherwise indicated, includes fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. It is understood that for said alkyl group to include cyclic moieties it must contain at least three carbon atoms.

The term "aryl", as used herein, unless otherwise indicated, includes an organic radical derived from an aromatic hydrocarbon by removal of one hydrogen, such as phenyl or naphthyl.

The term "4–10 membered heterocyclic", as used herein, unless otherwise indicated, includes aromatic and non-aromatic heterocyclic groups containing one or more heteroatoms each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3 -dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. In this regard, the invention includes both the E and Z configurations of the —CX¹R² moiety. The compounds of formula 1 may also exist as tautomers. This invention relates to the use of all such tautomers and mixtures thereof.

The present invention includes the compounds of the present invention, and the pharmaceutically acceptable salts thereof, wherein one or more hydrogen, carbon or other atoms are replaced by isotopes thereof. Such compounds may be useful as research and diagnostic tools in metabolism pharmacokinetic studies and in binding assays.

DETAILED DESCRIPTION OF THE INVENTION

The preparation of the compounds of the present invention is illustrated in the following Scheme.

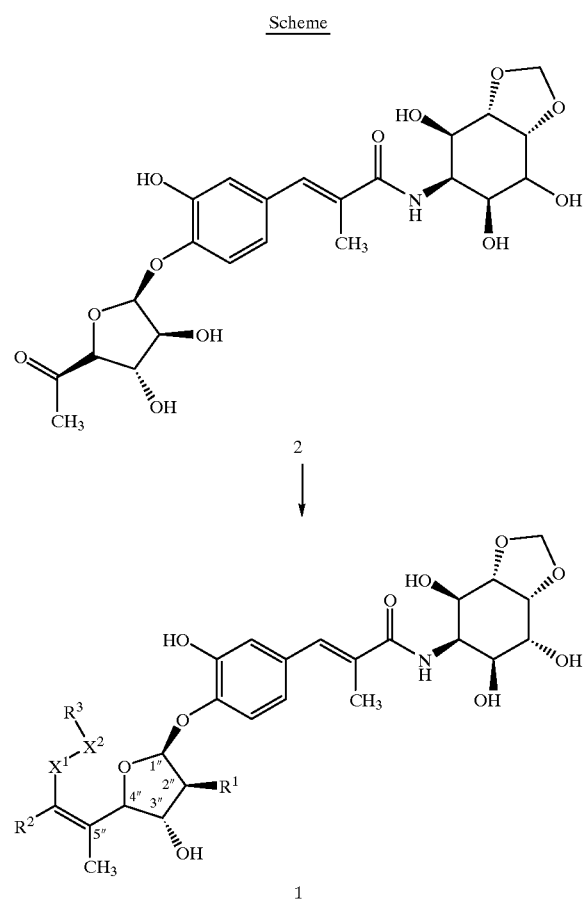

The compounds of the present invention are readily prepared. With reference to the Scheme illustrated above, the starting compound of formula 2 is hygromycin A which may be prepared according to procedures known to those skilled in the art, such as by fermentation of *Streptomyces hygroscopicus* NRRL 2388. The methyl ketone at 4" on the furanose sugar of the hygromycin A molecule can exist in the S configuration (hygromycin A) or R configuration (epi-hygromycin) on the furanose sugar. When published protocols are used as a model for fermentation and recovery of hygromycin A (U.S. Pat. No. 3,100,176; Antibiotic Chemotherapy (1953)3:1268–1278, 1279–1282), the hygromycin product is an approximately 3:1 mixture of hygromycin A (the 4"-(S) epimer), with the beta-oriented methyl ketone on the furanose sugar, as drawn, and epi-hygromycin. It is known in the literature (Journal of Antibiotics 33(7), 695–704, 1980) that pure hygromycin A will convert to epi-hygromycin in alkaline solutions. By carefully controlling the pH below 6.9 during the fermentation, and the pH, temperature and solvent exposure during the purification process, the final recovered product may be improved to at least a 14:1 ratio of hygromycin A:epi-hygromycin. Using this material, substantially single isomers derived from the 4"-(S) hygromycin may be prepared for use as templates for further synthetic modification.

Hygromycin A enriched for the 4"-(S) epimer is produced by fermentation of *Streptomyces hygroscopicus* NRRL 2388, or mutants thereof, in media with pH controlled at less than 6.9, preferably 6.2 to 6.7, throughout the process. The medium contains assimilable sources of carbon, nitrogen and trace elements, as known to those skilled in the art. The fermentation is run at a temperature of about 25–35° C., preferably about 29° C. The fermentation is monitored, for example by high pressure liquid chromatography. Incubation is continued until the yield of the compound reaches a maximum, generally for a period of about 3 to 10 days, preferably about 4 to 6 days.

The formation of epi-hygromycin is minimized during the purification process by using an aqueous buffer (rather than unbuffered water) and controlling the pH of the active streams to near 6.0. Epi-hygromycin formation is also minimized by minimizing the time the recovered material is subject to higher temperatures. Thus, where it is necessary to reduce solvent concentrations, it is preferred to dilute active streams with the aqueous buffer and avoid use of rotary evaporation at elevated temperatures. Also, as means of avoiding higher temperatures, a resin column may be used to concentrate the active solution prior to the final purification step in order to reduce the volume of solution that must be boiled. The final purification step in the process is the concentration of the active cuts to solids using vacuum and a bath temperature of about 35–50° C. The period in which the solution is subject to elevated temperatures may be minimized by boiling in stages.

The compound of formula 1 where R² is defined as above, X¹ is CH₂, X² is O and R³ is H may be prepared through the corresponding α,β-unsaturated ester intermediates derived from Wittig, Horner-Emmons or Peterson olefination of the C-5" ketone of hygromycin A. For instance, (carbethoxymethylene)triphenylphosphorane or (carbethoxyethylidene)triphenylphosphorane can be reacted with hygromycin A to provide the unsaturated ethyl ester. At this point the hydroxy groups of hygromycin A may be appropriately protected, for instance as their silyl ethers using an appropriate reagent such as triethylsilyl chloride (TESCl), trimethylsilyl chloride (TMSCl) or tert-butyldimethylsilyl chloride (TBDMSCl) and an amine base, such as imidazole or pyridine. This compound may then be reduced, for instance with diisobutyl aluminum hydride, and deprotection of the hydroxyl groups may be carried out by use of acid, such as acetic acid or fluoride ion, such as TBAF.

The compounds of formula 1 where R¹ is H and where R² is defined as above, X¹ is CH₂, X² is O and R³ is H can be prepared through the corresponding α,β-unsaturated ester intermediates derived from Wittig, Horner-Emmons or Peterson olefination of the C-5" ketone of 2"-deoxypentaprotected hygromycin A. In this process hygromycin A is prepared by protection of all of the hydroxy groups of hygromycin A, with the exception of the hydroxy at the 2" carbon (C-2"), as their silyl ethers using an appropriate reagent such as triethylsilyl chloride (TESCl), trimethylsilyl chloride (TMSCl) or tert-butyldimethysilyl chloride (TBDMSCl). The preferred method is 10 eq of TBDMSCl and imidazole in N,N-dimethylformamide (DMF) at a temperature of 25–40° C. for 12–36 hours. The 2"-deoxypentaprotected hygromycin A is then prepared by removal of the hydroxy group using the method of Barton et al., *J. Chem Soc., Perkin Trans. I* 1975, 1574. The preferred method in this case is the method of Génu-Dellac et al., *Carbohydrate Res.* 1991, 216, 249. The aforementioned α,β-unsaturated ester may then be prepared via a Wittig, Horner-Emmons or Peterson olefination of the C-5" ketone of 2"-deoxypentaprotected hygromycin A. For instance, (carbethoxymethylene)triphenylphosphorane or (carbethoxyethylidene)triphenyl-phosphorane can be reacted with hygromycin A to provide the unsaturated ethyl ester. This compound may then be reduced, for instance with diisobutyl aluminum hydride, and deprotection of the hydroxyl groups may be carried out by use of acid, such as acetic acid or fluoride ion, such as TBAF.

The compound of formula 1 where $R^1$ and $R^2$ are defined as above, $X^1$ is $CH_2$, $X^2$ is O and $R^3$ is —C(O)($CR^6R^7$)$_t$($C_6$–$C_{10}$ aryl), wherein $R^6$, $R^7$ and "t" are as defined above, may be prepared via acylation of protected hygromycin allyl alcohol described above; for example by treatment of said alcohol with X—C(O)($CR^6R^7$)$_t$($C_6$–$C_{10}$ aryl), wherein X is a leaving group such as Cl, Br or N-hydroxysuccinimide (NHS) ester, in the presence of a base, such as sodium hydride, triethylamine or potassium tert-butoxide. The protecting groups may then be removed as above.

The compound of formula 1 where $R^1$ and $R^2$ are defined as above, $X^1$ is $CH_2$, $X^2$ is O and $R^3$ is —($CR^6R^7$)$_t$($C_6$–$C_{10}$ aryl), wherein $R^6$, $R^7$ and "t" are as defined above, may be prepared via alkylation of protected hygromycin allyl alcohol described above; for example by treatment of said alcohol with X—($CR^6R^7$)$_t$($C_6$–$C_{10}$ aryl), wherein X is a leaving group such as Cl, Br or mesylate, in the presence of a base, such as sodium hydride, triethylamine or potassium tert-butoxide. The protecting groups may then be removed as above.

The compound of formula 1 where $R^1$ and $R^2$ are defined as above, $X^1$ is $CH_2$, $X^2$ is O or S, "t" is 0 and $R^3$ is —($CR^6R^7$)$_t$($C_6$–$C_{10}$ aryl), wherein $R^6$ and $R^7$ are as defined above, may also be prepared via a Mitsunobu reaction. The protected hygromycin allyl alcohol, prepared as described above, is subjected to a Mitsunobu reaction with HO—($CR^6R^7$)$_t$($C_6$–$C_{10}$ aryl) or HS—($CR^6R^7$)$_t$($C_6$–$C_{10}$ aryl), mediated by triphenylphosphine and diethyl azodicarboxylate as described in D. L. Hughes, Org. Reactions (1992) 42 335. The resulting ether or thioether may then be deprotected as described above or in the case of the thioether may be oxidized, for instance with m-CPBA, and then deprotected as described above.

The compound of formula 1 where $R^1$ and $R^2$ are defined as above, $X^1$ is $CH_2$, $X^2$ is O and $R^3$ is —C(O)$NR^6$($CR^6R^7$)$_t$($C_6$–$C_{10}$ aryl), wherein $R^6$, $R^7$ and "t" are defined above, may be prepared by reacting protected hygromycin allyl alcohol, prepared as described above, with isocyanate $OCNR^6$($CR^6R^7$)$_t$($C_6$–$C_{10}$ aryl), in toluene at temperatures from 40° C. to 110° C., preferably 50–80° C. Addition of dimethylaminopyridine and triethylamine to the reaction may be advantageous. The protecting groups may then be removed as above.

The compound of formula 1 where $R^1$ and $R^2$ are defined as above, $X^1$ is $CH_2$, $X^2$ is N and $R^3$ is defined as above, with the proviso that nitrogen is not adjacent to a carbonyl functionality, may be prepared via reduction amination of protected hygromycin aldehyde, prepared by the oxidation of the allyl alcohol above: (1) the allyl alcohol may be oxidized, for example using Swern conditions as described in T Tidwell, Org. Reactions (1990) 39 297, (2) and combined with $HN(R^6)$—$R^3$ in an inert solvent and then (3) treated with a reducing agent such as $NaBH_4$, $NaBH(OAc)_3$ (Ac is acetyl), or $NaCNBH_3$. $R^6$ may be introduced as part of $HN(R^6)$—R3 in step (2) or introduced after step (3), wherin $H_2NR^3$ was used, via alkylation, for instance with a base such as sodium hydride or potassium tert-butoxide and an alkylating agent such as $R^6$—X where is X is Br, Cl or methanesulfonate.

The compound of formula 1 where $R^1$ and $R^2$ are defined as above, $X^1$ is $NR^6$, S or $S(O)_n$, $X^2$ is C or $NR^6$ and $R^3$ is —($CR^6R^7$)$_t$($C_6$–$C_{10}$ aryl), wherein $R^6$, $R^7$ and "t" are defined above, may be prepared by the Peterson Olefination reaction as described in D. Ager, Org. Reactions (1990) 38 1. For example, protected hygromycin ketone, prepared by reacting the appropriate reagent such as triethylsilyl chloride (TESCl), trimethylsilyl chloride (TMSCl) or tert-butyldimethylsilyl chloride (TBDMS) and imidazole or pyridine with hygromycin A, may be reacted with TMS—CH($R^2$)—$X^1$—$X^2$—$R^3$ in the presence of a strong base, for example lithium diisopropylamide or butyl lithium. When the intermediate β-hydroxysilane is stable the olefin may be generated by further reaction with strong base, for example sodium or potassium hydride. The protecting groups may then be removed as above. TMS—CH($R^2$)—$X^1$—$X^2$—$R^3$, where $X^1$ is S or $S(O)_n$, may be made from trimethylsilylmethylsulfide, for example by reaction with the appropriate electrophile in the presence of an amine base, such as triethylamine or pyridine. The thiol may be oxidized by m-CPBA to the sulfone. TMS—CH($R^2$)—$X^1$—$X^2$—$R^3$, where $X^1$ is $S(O)_n$ and $X^2$ is $NR^6$, may be prepared from trimethylsilylmethanesulfonyl chloride and the appropiate amine, $HN(R^6)$—($CR^6R^7$)$_t$($C_6$–$C_{10}$ aryl).

The compound of formula 1 where $R^1$ and $R^2$ are defined above, $X^1$ is C and where $X^2$ is N and $X^2$ and $R^3$ are taken together as described above may be prepared by the reaction of $HNR^6R^3$ with protected hygromycin allyl mesylate in the presence of an amine base, such as triethylamine or pyridine. Protected hyrgromycin allyl mesylate may be prepared by the reaction of protected hygromycin allyl alcohol, described above, with methanesulfonyl chloride in the presence of an amine base, such as triethylamine or pyridine.

The compounds of the present invention have asymmetric carbon atoms. Compounds having a mixture of isomers at one or more centers will exist as diastereomeric mixtures, which can be separated into their individual diastereomers on the basis of their physical chemical differences by methods known to those skilled in the art, for example, by chromatography or fractional crystallization. All such isomers, including diastereomer mixtures, are considered as part of the invention.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the basic compounds of this invention are readily prepared by treating the basic compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium, calcium and magnesium, etc. These salts can easily be prepared by treating the corresponding acidic compounds with an aqueous solution containing the desired alkali metal alkoxide or metal hydroxide, and then evaporating the resulting solution to dryness, preferably under reduced pressure. Alternatively, they may also be prepared by mixing lower alkanolic solutions of the acidic compounds and the desired alkali metal alkoxide or metal hydroxide together, and then evaporating the resulting solution to dryness in the same manner as before. In either case, stoichiometric quantities of reagents are preferably employed in order to ensure completeness of reaction and maximum yields of the desired final product.

The antibacterial activity of the compounds of the present invention against bacterial pathogens is demonstrated by the compound's ability to inhibit growth of defined strains of pathogens.

ASSAY

The assay, described below, employs conventional methodology and interpretation criteria and is designed to provide direction for chemical modifications that may lead to compounds with antibacterial activity against susceptible and drug-resistant organisms including, but not limited to, beta-lactam, macrolide and vancomycin resistance. In the assay, a panel of bacterial strains is assembled to include a variety of target pathogenic species, including representatives of antibiotic resistant bacteria. Use of this panel enables the chemical structure/activity relationship to be determined with respect to potency and spectrum of activity. The assay is performed in microtiter trays and interpreted according to *Performance Standards for Antimicrobial Disk Susceptibility Tests—Sixth Edition; Approved Standard*, published by The National Committee for Clinical Laboratory Standards (NCCLS) guidelines; the minimum inhibitory concentration (MIC) is used to compare strains. Compounds are initially dissolved in dimethylsulfoxide (DMSO) as stock solutions.

The activity of the compounds of the present invention also may be assessed in accord with Steers replicator technique which is a standard in vitro bacterial testing method described by Steers et al., *Antibiotics and Chemotherapy* 1959, 9, 307.

The in vivo activity of the compounds of the present invention can be determined by conventional animal protection studies well known to those skilled in the art, usually carried out in rodents.

According to one in vivo model, compounds are evaluated for efficacy in mouse models of acute bacterial infection. An example of one such in vivo system is provided as follows. Mice (CF1 mixed sex mice; 18–20 g) are allotted to cages upon their arrival, and allowed to acclimate 1–2 days before being placed in a study. The acute infection is produced by intraperitoneal inoculation of bacteria (*Staphylococcus aureus* strain 01A1095) suspended in 5% sterile hog gastric mucin. The inoculum is prepared by: growing the culture overnight at 37° C. on blood agar, harvesting the resulting surface growth with sterile brain heart infusion broth, and adjusting this suspension to a turbidity that when diluted 1:10 into 5% sterile hog gastric mucin would produce 100% lethality.

Mice (10 per group) are treated subcutaneously, at 0.5 hour and 4 hours after challenge. Appropriate non-treated (infected but not treated) and positive (vancomycin or minocycline, etc.) controls are included in each study. Percent survival is recorded after a 4-day observation period; the $PD_{50}$ (mg/kg/dose calculated to protect 50% of infected animals) is determined by the probit method.

The compounds of the present invention, and the pharmaceutically acceptable salts thereof (hereinafter "the active compounds"), may be administered through oral, parenteral, topical, or rectal routes in the treatment of bacterial and protozoal infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 3 mg/kg/day to about 60 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral adinistration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous ethanol or propylene glycol may be employed. Use of a cyclodextrin derivative such as β-cyclodextrin sulfobutyl ether, sodium salt (see U.S. Pat. No. 5,134,127) may also be advantageous. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The present invention is further described and exemplified in the preparations and examples described below. In the preparations and examples, "rt" means room or ambient temperature which is a temperature within the range of about 20–25° C.

Preparation 1

Five (5) mL of a frozen lot (stored at −80° C. in 20% glycerol/80% inoculum medium) of the culture *Streptomyces hygroscopicus* NRRL 2388 was used to inoculate 1 L of hygromycin inoculum medium (Corn Products Corp. cerelose 13 g/L, Hubinger starch 7 g/L, Roquette corn steep solids 3 g/L, Sheffield Brand Products NZ Amine YTT 7 g/L, Baker $CoCl_2.6H_2O$ 0.002 g/L, $KH_2PO_4$ 0.7 g/L, $MgSO_4.7H_2O$ 1.3 g/L, ammonium sulfate 0.7 g/L, Dow Chemical P2000 defoamer 1 drop/flask, Colfax soybean oil 2 drops/flask, pH to 7.0 before autoclave) in a 2.8 L Fernbach flask. The culture was grown for 3 days at 29° C. with 200 rpm agitation on a 2-inch-throw shaker. This grown culture was used to inoculate 8 L of sterile hygromycin fermentation medium (Albaglos calcium carbonate 1 g/L, Sheffield Brand Products NZ Amine YTT 5 g/L, Hubinger's starch 20 g/L, Archer Daniels Midland Nutrisoy flour 10 g/L, Dow Chemical P2000 defoamer 1 ml/L, Baker $CoCl_2.6H_2O$ 0.002 g/L, Colfax soybean oil 2 ml/L, cerelose 10 g/L, NaCl 5 g/L, pH to 7.0 before autoclave) in a 14 liter fermentor jar (New Brunswick Microferm, New Brunswick, N.J.) equipped with two 4.75-inch Rushton impellers, spaced 3.75 inches from each other. The broth was incubated at 29° C. with an aeration rate of 8 L/minute, and with stirring at 800 rpm. To minimize formation of epi-hygromycin, the pH was maintained between 6.5 and 6.9 for 126 hours, then to 6.2 to 6.6 with $H_2SO_4$ (15%) for the rest of the run. The fermentation was harvested after 143 hours total incubation. At this time, the ratio was 31:1 hygromycin A to epi-hygromycin.

Six liters of broth from the above fermentation was centrifuged at 8000 rpm for approximately 15 minutes. After centrifugation, the pellet was discarded and the supernatant (at pH 6.4, assayed by HPLC to contain approximately 4.12 gms of hygromycin A activity) was loaded on a column packed with 500 gms of an XAD-16 resin (Rohm and Haas (Philadelphia, Pa.). The resin had previously been equilibrated with two bed volumes of 25 mM disodium phosphate, pH 6.0 ("buffer"). After loading, the column was washed with 2 bed volumes of buffer and 2 bed volumes of 80/20 buffer/methanol and the activity eluted with 5 bed volumes of 50/50 buffer/methanol. The cuts were assayed by HPLC and the cuts containing the bulk of the activity (2.730 gms of hygromycin A) were combined.

A part of this XAD-16 eluate (approximately 800 mg of hygromycin A) was diluted to 10% methanol by the addition of 1.8 liters of buffer and loaded on a 100 ml CG-161 column (TosoHaas (Montgomeryville, Pa.)) which had been equilibrated with 4 bed volumes of 90/10 buffer/methanol. The product was eluted with 6 bed volumes of 50/50 buffer/methanol. The cuts were assayed by HPLC and the active cuts were combined. The combined cut was evaporated to dryness and the solids assayed to be approximately 65% pure by weight. A small part of these solids were transferred for assay.

About 500 mg of the solids were mixed with 500 ml of water and 500 ml of ethyl acetate and stirred for 20 minutes. The two layers were separated and part of the aqueous layer was dried to obtain solids which were assayed to be approximately 52% purity by weight. Both these solids (#34945-280-1 and 281-1) were assayed by NMR and TLC and found to contain hygromycin A activity. In addition, the NMR showed a hygromycin A/epi-hygromycin ratio of approximately 15:1.

Preparation 2

Five (5) mL of a frozen lot (stored at −80° C. in 20% glycerol/80% inoculum medium) of the culture *Streptomyces hygroscopicus* NRRL 2388 was used to inoculate 1 L of Hygromycin inoculum medium (CPC International Inc. cerelose 13 g/L, Hubinger's starch 7 g/L, Roquette corn steep solids 3 g/L, NZ Amine YTT 7 g/L, Baker $CoCl_2.6H_2O$ 0.002 g/L, $KH_2PO_4$ 0.7 g/L, $MgSO_4.7H_2O$ 1.3 g/L, ammonium sulfate 0.7 g/L, Dow Chemical P2000 defoamer 1 drop/flask, Colfax soybean oil 2 drops/flask, pH to 7.0 before autoclave) in a 2.8 L Fernbach flask. The culture was grown for 2 to 3 days at 29° C. with 200 rpm agitation on a 2-inch-throw shaker. Two five-hundred gallon, stainless steel fermentors were loaded with 380–400 gallons of the hygromycin fermentation medium (Mineral Technologies Calcium Carbonate 1 g/L, Sheffield Brand Products NZ Amine YTT 5 g/L, Hubinger's starch 20 g/L, Archer Daniels Midland Co., Soyflour 10 g/L, Dow Chemical P2000 defoamer 1 ml/L, Baker $CoCl_2.6H_2O$ 0.002 g/L, Colfax, Inc. soybean oil 2 gm/L, CPC International Inc. Cerelose 10 g/L, Cargill Inc. NaCl 5 g/L,). The medium was sterilized with 20 psig of steam for 60 minutes in the fermentors. After the medium was cooled using cooling coils in the fermentors, the pH was adjusted to 6.5–6.7. The fermentor conditions were set so that the airflow rate was 20 standard cubic feet per minute, the temperature was 28° C., the vent pressure was 5 psig, and the pH was maintained between 6.5–6.7 with 25% sodium hydroxide and 98% sulfuric acid. The agitation rates in the two fermentors were varied so as to maintain a dissolved oxygen level of greater than 20% of saturation level as measured in the broth immediately prior to inoculation. Upon setting the fermentor control conditions, five Fernbach inoculum flasks were combined in a sterile manner, into an 8 L aspirator bottle. This inoculum was then used for inoculation of a single, nominal, five-hundred gallon fermentor as described above. This procedure was repeated using 4 liters of inoculum so that one fermentor received four liters of inoculum and one fermenter received five liters of inoculum. Each fermentor ran for approximately 114 hours, at which time the fermentations were stopped. The broth pH was adjusted to 6.3 using 98% sulfuric acid and transferred from the fermentors for recovery.

The two fermentors referred to above (pH=6.3, having a ratio of hygromycin A to epi-hygromycin of approximately 51:1) were filtered on a ceramic filtration system. The filtrate (1450 gmsA, 506 gal) was loaded on a 70-gallon XAD-16 resin column. This column had been equilibrated previously with 4 bed volumes of a solution of trisodium phosphate buffer at pH 6.0 ("buffer"). After loading, the column was washed with 2 bed volumes of buffer and 2 bed volumes of 80/20 buffer/methanol. The activity was subsequently eluted from the column with 10 cuts (approximately 50 gallons each) of a solution of 50/50 buffer/methanol. The active cuts (approximately 1240 gmsA) were combined and diluted to a final concentration of 10% methanol by the addition of 1200 gallons of buffer. The use of dilution (rather than rotary evaporation) to reduce methanol concentration allowed the use of lower temperatures so as to minimize epi-hygromycin amounts, which tend to increase at higher temperatures. Half of this solution was loaded on a 40 liter CG-161 column (previously equilibrated with 4 bed volumes of a solution of 90/10 buffer/methanol). After loading, the column was washed with 4 bed volumes of 80/20 buffer/methanol and eluted with 5.5 bed volumes of 50/50 buffer/methanol. After regeneration and re-equilibration of the column, the second half of the activity was loaded on the column and eluted as described above. The combined cuts from both the runs (120 liters, approximately 1051 gmsA) were diluted to 10% methanol by the addition of buffer. This was re-loaded on the regenerated and re-equilibrated CG-161 resin column. Once the activity was adsorbed on the column, it was eluted with 4 bed volumes of methanol. This step served to both reduce the salts as well as increase the concentration of the sample prior to the final evaporation. The combined cuts from the final CG-161 column were evaporated to dryness to obtain a total of approximately 1 kgA of hygromycin A activity. The ratio of hygromycin A to epi-hygromycin in the final solids was about 14.5:1.

EXPERIMENTAL PROCEDURES FOR EXAMPLES

5"-Allyl Alcohol Preparations

1. Preparation of E-Allyl Alcohol via Wittig Reaction
Method A

A solution of hygromycin A (1 eq.) and carboethoxymethylene triphenylphosphorane (2 eq.) in DMF (roughly 0.5 M in hygromycin) was allowed to stir at 70° C. for 5 hours and allowed to cool to room temperature. Imidazole (12 eq.) and tert-butyldimethylsilyl chloride (12 eq.) were added and the reaction was allowed to stir at 80° C. for 15 hours. The reaction was diluted with hexanes and diethyl ether (roughly 1:1), washed with water, then saturated sodium chloride solution, dried over magnesium sulfate, filtered and concentrated. The crude product was purified by silica gel chromatography, eluting with 10% ethyl acetate in hexanes.

A solution of the ethyl ester of hygromycin A (1 eq.) in methylene chloride (roughly 0.1M) at −78° C. was treated with diisobutyl aluminum hydride (4 eq.). After treatment with saturated Rochelle's salt and warming to room temperature the reaction was diluted with methylene chloride, washed with saturated ammonium chloride, then saturated sodium chloride, dried over magnesium sulfate, filtered, and concentrated. The crude product was purified by silica gel chromatography, eluting with a step gradient of 5% ethyl acetate in hexanes to 33% ethyl acetate in hexanes.

2. Preparation of E and Z-Allyl Alcohol via Peterson Reaction

Method B

A solution of hygromycin A (1 eq.), tert-butyldimethylsilyl chloride (12 eq.), and imidazole (12 eq.) in DMF (hygromycin concentration 0.25 M) was stirred at 80° C. for 20 hours. After removal of the DMF under reduced pressure, the resulting residue was extracted with diethyl ether. The combined ether extracts were washed with water, then saturated sodium chloride solution, dried over sodium sulfate, filtered, and concentrated. The crude product was purified by silica gel chromatography, eluting with 10% ethyl acetate in hexanes.

A solution of ethyl (trimethylsilyl)acetate (4 eq.) in THF (roughly 0.4 M in ethyl (trimethylsilyl)acetate) at −78° C. was treated with lithium diisopropylamide (3.5 eq.). After 30 minutes a solution of persilylated hygromycin A (1 eq.) in THF (roughly 0.5 M) was added. After 15 minutes the reaction was diluted with ethyl acetate and saturated ammonium chloride solution. The organic layer was washed with saturated ammonium chloride solution, then saturated sodium chloride solution, dried over magnesium sulfate, filtered and concentrated. A solution of this crude ethyl ester (1 eq.) in methylene chloride (roughly 0.1M) at −78° C. was treated with diisobutyl aluminum hydride (8 eq.). After treatment with saturated Rochelle's salt and warming to room temperature the reaction was diluted with methylene chloride, washed with saturated ammonium chloride, then saturated sodium chloride, dried over magnesium sulfate, filtered, and concentrated. The crude product was purified by silica gel chromatography, eluting with a step gradient of 5% ethyl acetate in hexanes to 33% ethyl acetate in hexanes to provide a mixture of E and Z allylic alcohols.

Method C

A solution of hygromycin A (1 eq.), tert-butyldimethylsilyl chloride (12 eq.), and imidazole (12 eq.) in DMF (hygromycin concentration 0.25 M) were stirred at 80° C. for 20 hours. After removal of the DMF under reduced pressure, the resulting residue was extracted with diethyl ether. The combined ether extracts were washed with water, then saturated sodium chloride solution, dried over sodium sulfate, filtered, and concentrated. The crude product was purified by silica gel chromatography, eluting with 10% ethyl acetate in hexanes.

A solution of methyl 2-(trimethylsilyl)propionate (5 eq.) in THF (roughly 0.2 M methyl 2-(trimethylsilyl)propionate) at −78° C. was treated with lithium diisopropylamide (4 eq.). After 30 minutes a solution of persilylated hygromycin A (1 eq.) in THF (roughly 0.4 M) was added. After 15 minutes the reaction was diluted with ethyl acetate and saturated ammonium chloride solution. The organic layer was washed with saturated ammonium chloride solution, then saturated sodium chloride solution, dried over magnesium sulfate, filtered and concentrated. A solution of this crude ethyl ester (1 eq.) in methylene chloride (roughly 0.1 M) at −78° C. was treated with diisobutyl aluminum hydride (8 eq.). After treatment with saturated Rochelle's salt solution and warming to room temperature the reaction was diluted with methylene chloride, washed with saturated ammonium chloride solution, then saturated sodium chloride solution, dried over magnesium sulfate, filtered, and concentrated. The crude product was purified by silica gel chromatography, eluting with a step gradient of 5% ethyl acetate in hexanes to 33% ethyl acetate in hexanes to provide a mixture of E and Z allylic alcohols.

Protected 5"-Allyl Derivative Preparations

Method D (Examples 2–6)

Silylated hygromycin A allyl alcohol (1 eq.) in dioxane (roughly 0.03 M) was treated with the appropiate benzyl halide (5 eq.) and potassium tert-butoxide (2 eq.). After completion (roughly 10 minutes) the reactions were diluted with ethyl acetate and 0.05 M pH 7.0 phosphate-sodium hydroxide buffer solution. The organic layers were washed with saturated sodium chloride solution, dried over magnesium sulfate, filtered, and concentrated. The crude products were purified by silica gel chromatography, eluting with a step gradient of 5% ethyl acetate in hexanes to 33% ethyl acetate in hexanes.

The persilated allyl ethers were deprotected and purified by method H.

Method E (Examples 7–11)

Silylated hygromycin allyl alcohol (1 eq.) in methylene chloride (roughly 0.03 M) was treated with the appropiate benzoyl halide (4 eq.) and triethylamine (10 eq.). After completion (roughly 30 minutes to 1 hour) the reactions were diluted with methylene chloride and 0.05 M pH 7.0 phosphate-sodium hydroxide buffer solution. The organic layers were dried over magnesium sulfate, filtered, and concentrated. The crude products were purified by silica gel chromatography, eluting with a step gradient of 5% ethyl acetate in hexanes to of 33% ethyl acetate in hexanes.

The persilated allyl esters were deprotected and purified by method H.

Method F (Examples 12, 13)

Silylated hygromycin allyl alcohol (1 eq.) in toluene (roughly 0.03 M) was treated with the appropiate isocyanate (5 eq.) and triethylamine (3 eq.). After completion (roughly 30 minutes to 4 hours) the reactions were diluted with ethyl acetate and 0.05 M pH 7.0 phosphate-sodium hydroxide buffer solution. The organic layers were washed with saturated sodium chloride solution, dried over magnesium sulfate, filtered, and concentrated. The crude products were purified by silica gel chromatography, eluting with a step gradient of 5% ethyl acetate in hexanes to 33% ethyl acetate in hexanes.

The persilated allyl carbamates were deprotected and purified by method H.

Method G (Examples 14–57)

Silylated hygromycin allyl alcohol (1 eq.) in toluene (roughly 0.03 M) was treated with the appropiate phenol (3–5 eq.), triphenylphosphine (3–5 eq.) and diethyl azodicarboxylate (3–5 eq). After completion (roughly 30 minutes to 2 hours) the reactions were diluted with ethyl acetate and 0.05 M pH 7.0 phosphate-sodium hydroxide buffer solution. The organic layers were washed with saturated sodium chloride solution, dried over magnesium sulfate, filtered, and concentrated.

In those cases where methods B, C or J were used to prepare the allylic alcohol the E and Z olefin mixtures were separated at this point by silica gel chromatography, eluting with a step gradient of 5% ethyl acetate in hexanes to 33% ethyl acetate in hexanes.

The crude (from method A) or pure allyl ethers (from methods B or C) were deprotected and purified by method H.

5"-Allyl Derivative Preparations

Method H

The silyl groups were removed by treatment of a solution of 5"-modified hexasilylhygromycin A in THF (roughly 0.1M) with a solution of HF•pyridine/pyridine/THF for 30 to 45 hours at room temperature. The reactions were diluted with ethyl acetate, treated with solid $NaHCO_3$, filtered, concentrated and purified by silica gel chromatography, eluting with a step gradient of 5% methanol in methylene chloride to of 33% methanol in methylene chloride.

5"-Allyl-2"-Deoxy Alchohol Preparation

1. Preparation of 2"-Deoxy-E-Allyl Alcohol via Wittig Reaction

Method I

A solution of hygromycin A (1 eq.) in dimethylformamide (DMF, 0.1 M) was treated with imidazole (10 eq) and tert-butyldimethylsilyl chloride (10 eq) at 35° C. for 14–16 hours. The reaction was poured into water and extracted with ethyl acetate (EtOAc). The combined extracts were dried over MgSO4 and concentrated. The product was obtained after chromatography eluting with a step gradient of 5% ethyl acetate in hexanes to of 15% ethyl acetate in hexanes. A solution of the compound (1 eq.) in dichloroethane was treated with phenylthionochloroformate (3 eq.), pyridine (5 eq) and dimethylaminopyridine (0.05 eq.) at room temperature for 2–3 days. At the end of this time the reaction was diluted with methylene chloride, washed with 0.5 N HCl, saturated sodium bicarbonate and then brine. The organics were dried over $MgSO_4$ and concentrated. The desired 2"-thionocarbonate was obtained after chromatography, eluting with a step gradient of 5% ethyl acetate in hexanes to of 10% ethyl acetate in hexanes. A solution of the above 2"-thionocarbonate (1 eq.) in toluene (0.1 M) was treated with α,α'-azobis(isobutyronitrile) (1 eq.) and tri-n-butyltinhydride (3 eq.) at 90° C. for 2 hours. The reaction was concentrated and chromatographed, eluting with a step gradient of 5% ethyl acetate in hexanes to of 10% ethyl acetate in hexanes, to provide the desired 2"-deoxy ketone.

A solution of penta-silyl protected hygromycin A (1 eq.) and carboethoxymethylene triphenylphosphorane (2 eq.) in DMF (roughly 0.5 M in hygromycin) was allowed to stir at 70° C. for 12 hours and allowed to cool to room temperature. Imidazole (1 eq.) and tert-butyldimethylsilyl chloride (1 eq.) were added and the reaction was allowed to stir at 70° C. for 4 hours. The reaction was diluted with hexanes and diethyl ether (roughly 1:1), washed with water, then saturated sodium chloride solution, dried over magnesium sulfate, filtered and concentrated. The crude product was purified by silica gel chromatography, eluting with a step gradient of 5% ethyl acetate in hexanes to 33% ethyl acetate in hexanes. A solution of the ethyl ester of hygromycin A (1 eq.) in methylene chloride (roughly 0.1M) at −78° C. was treated with diisobutyl aluminum hydride (4 eq.). After treatment with saturated Rochelle's salt and warming to room temperature the reaction was diluted with methylene chloride, washed with saturated ammonium chloride, then saturated sodium chloride, dried over magnesium sulfate, filtered, and concentrated. The crude product was purified by silica gel chromatography, eluting with a step gradient of 5% ethyl acetate in hexanes to 33% ethyl acetate in hexanes.

2. Preparation of 2"-Deoxy E- and Z-Allyl Alcohols via Peterson Reaction

Method J

A solution of hygromycin A (1 eq.) in dimethylformamide (DMF, 0.1 M) was treated with imidazole (10 eq) and tert-butyldimethylsilyl chloride (10 eq) at 35° C. for 14–16 hours. The reaction was poured into water and extracted with ethyl acetate (EtOAc). The combined extracts were dried over MgSO4 and concentrated. The product was obtained after chromatography eluting with a step gradient of 5% ethyl acetate in hexanes to of 15% ethyl acetate in hexanes. A solution of the compound (1 eq.) in dichloroethane was treated with phenylthionochloroformate (3 eq.), pyridine (5 eq) and dimethylaminopyridine (0.05 eq.) at room temperature for 2–3 days. At the end of this time the reaction was diluted with methylene chloride, washed with 0.5 N HCl, saturated sodium bicarbonate and then brine. The organics were dried over $MgSO_4$ and concentrated. The desired 2"-thionocarbonate was obtained after chromatography, eluting with a step gradient of 5% ethyl acetate in hexanes to of 10% ethyl acetate in hexanes. A solution of the above 2"-thionocarbonate (1 eq.) in toluene (0.1 M) was treated with α,α'-azobis(isobutyronitrile) (1 eq.) and tri-n-butyltinhydride (3 eq.) at 90° C. for 2 hours. The reaction was concentrated and chromatographed, eluting with a step gradient of 5% ethyl acetate in hexanes to of 10% ethyl acetate in hexanes, to provide the desired 2"-deoxy ketone.

A solution of ethyl (trimethylsilyl)acetate (4 eq.) in THF (roughly 0.4 M in ethyl (trimethylsilyl)acetate) at −78° C. was treated with lithium diisopropylamide (3.5 eq.). After 30 minutes a solution of 2"-deoxy persilylated hygromycin A (1 eq.) in THF (roughly 0.5 M) was added. After 15 minutes the reaction was diluted with ethyl acetate and saturated ammonium chloride solution. The organic layer was washed with saturated ammonium chloride solution, then saturated sodium chloride solution, dried over magnesium sulfate, filtered and concentrated. A solution of this crude ethyl ester (1 eq.) in methylene chloride (roughly 0.1M) at −78° C. was treated with diisobutyl aluminum hydride (8 eq.). After treatment with saturated Rochelle's salt and warming to room temperature the reaction was diluted with methylene chloride, washed with saturated ammonium chloride, then saturated sodium chloride, dried over magnesium sulfate, filtered, and concentrated. The crude product was purified by silica gel chromatography, eluting with a step gradient of 5% ethyl acetate in hexanes to 33% ethyl acetate in hexanes to provide a mixture of E and Z allylic alcohols.

2"-Deoxy-5"-Allyl Derivative Preparations

Examples 58–73 were prepared in an analogous fashion as examples 14–57. Protected 2"-deoxy-5"-allyl ether derivatives were prepared using method G and subsequently deprotected using method H.

The following compounds were prepared using the synthetic methods described above:

3-(4-((2S,3S,4S,5R)-3,4-Dihydroxy-5-(3-hydroxy-1-methyl-(1E)-propenyl)-tetrahydro-furan-2-yloxy)-3-hydroxy-phenyl)-2-methyl-N-((3aS,4R,5R,6S,7R,7aR)-4,6,7-trihydroxy-benzo(1,3)dioxol-5-yl)-(2E)-acrylamide;

3-(4-((2S,3S,4S,5R)5-(3-Benzyloxy-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-benzo(1,3)dioxol-5-yl)-(2E)-acrylamide;

3-(4-((2S,3S,4S,5R)5-(3-(3-Chloro-benzyloxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-benzo(1,3)dioxol-5-yl)-(2E)-acrylamide;

3-(4-((2S,3S,4S,5R)5-(3-(Biphenyl-2-ylmethoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-benzo(1,3)dioxol-5-yl)-(2E)-acrylamide;

3-(4-((2S,3S,4S,5R)5-(3-(4-tert-Butyl-benzyloxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-benzo(1,3)dioxol-5-yl)-(2E)-acrylamide;

3-(4-((2S,3S,4S,5R)5-(3-(4-Fluoro-benzyloxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-benzo(1,3)dioxol-5-yl)-(2E)-acrylamide;

Benzoic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

4-Methoxy-benzoic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

2-Fluoro-benzoic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

3-Chloro-benzoic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

4-Trifluoromethyl-benzoic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

Benzyl-carbamic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

Phenyl-carbamic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

3-(4-((2S,3S,4S,5R)-5-(3-(3-Chloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3-Fluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3,5-Difluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Fluoro-phenoxy)-1-methyl-(1E)-propenyl)-3,4-dihydroxy-tetrahydro-furan-2-yloxy)-3-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Chloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-4-fluro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Chloro-3-fluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3,5-Dichloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3-chloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(pyridin-3-yloxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3-chloro-4-fluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3-Methoxy-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,4-Dichloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,4-Difluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-chloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,6-Difluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3-chloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Fluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Fluoro-2-propyl-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-phenoxy-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Benzyl-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Benzoyl-4-chloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Cyano-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(Indan-4-yloxy)-1-methyl-(1E)-propenyl)-3,4-dihydroxy-tetrahydro-furan-2-yloxy)-3-hydroxy-phenyl)-2-methyl-N-(3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Chloro-2-fluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,6-Dichloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-4-fluoro-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-5-fluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,3,4-Trichloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,3-Dichloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,5-Dichloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,5-Dichloro-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Fluoro-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,4-Dichloro-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-5-fluoro-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5yl)-(2E)-acrylamide;

3-(4-((2S,3S,4S,5R)-5-(3-(2-Chloro-3,5-difluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-3,5-difluoro-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,4,5-Trichloro-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,4,5-Trichloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Fluoro-2-trifluoromethyl-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Fluoro-2-trifluoromethyl-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Trifluoromethyl-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Trifluoromethyl-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-4-fluoro-phenoxy)-1,2-dimethyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-phenoxy)-1,2-dimethyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2-Chloro-4-fluoro-phenoxy)-1-methyl-(1Z)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2-Chloro-4-fluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,3-Dichloro-4-fluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,3,4-trichloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,4,5-trichloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,5-Dichloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(3-Chloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(3-Fluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,4-Difluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2-Chloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,4-Dichloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2-Chloro-5-fluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2-Chloro-3,5-difluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(3,5-Difluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(3-Fluoro-4-chloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2-Fluoro-4-chloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide.

The following compounds can be made by one skilled in the art using the general and specific synthetic methods described above:

3-(4-{(2S,3S,4S,5R)-5-[3-(Benzothiazol-6-yloxy)-1-methyl-(1E)-propenyl]-3,4-dihydroxy-tetrahydro-furan-2-yloxy}-3-hydroxy-phenyl)-2-methyl-N- ((3aS,4R,5R,6S,7R,7aR)-4,6,7-trihydroxy-hexahydro-benzo[1,3]dioxol-5-yl)-acrylamide;

3-(4-{(2S,3S,4S,5R)-5-[3-(Benzothiazol-6-yloxy)-1-methyl-(1Z)-propenyl]-3,4-dihydroxy-tetrahydro-furan-2-yloxy}-3-hydroxy-phenyl)-2-methyl-N- ((3aS,4R,5R,6S,7R,7aR)-4,6,7-trihydroxy-hexahydro-benzo[1,3]dioxol-5-yl)-acrylamide;

3-(4-{(2S,3S,4S,5R)-5-[3-(2-Chloro-pyridin-3-yloxy)-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-acrylamide;

3-(4-{(2S,3S,4S,5R)-5-[3-(2-Chloro-pyridin-3-yloxy)-1-methyl-(1Z)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-acrylamide;

3-[4-((2S,3S,4S,5R)-5-{3-[2,4-Dichloro-6-(methoxyimino-methyl)-phenoxy]-1-methyl-(1E)-propenyl}-3,4-dihydroxy-tetrahydro-furan-2-yloxy)-3-hydroxy-phenyl]-2-methyl-N-((3aS,4R,5R,6S,7R,7aR)-4,6,7-trihydroxy-hexahydro-benzo[1,3]dioxol-5-yl)-(2E)-acrylamide;

3-[4-((2S,3S,4S,5R)-5-{3-[2,4-Dichloro-6-(methoxyimino-methyl)-phenoxy]-1-methyl-(1Z)-propenyl}-3,4-dihydroxy-tetrahydro-furan-2-yloxy)-3-hydroxy-phenyl]-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-(2-Acetyl-4,6-dichloro-phenoxy)-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-(2-Acetyl-4,6-dichloro-phenoxy)-1-methyl-(1Z)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-3,4-Dihydroxy-5-[3-(1H-indol-5-yloxy)-1-methyl-(1E)-propenyl]-tetrahydro-furan-2-yloxy}-3-hydroxy-phenyl)-2-methyl-N- ((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-3,4-Dihydroxy-5-[3-(1H-indol-5-yloxy)-1-methyl-(1Z)-propenyl]-tetrahydro-furan-2-yloxy}-3-hydroxy-phenyl)-2-methyl-N- ((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-(2-Benzooxazol-2-yl-phenoxy)-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-acrylamide;

3-(4-{(2S,3S,4S,5R)-5-[3-(2-Benzothiazol-2-yl-phenoxy)-1-methyl-(1Z)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-5-(3-Benzenesulfonyl-1-methyl-(1E)-propenyl)-3,4-dihydroxy-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-5-(3-Benzenesulfonyl-1-methyl-(1Z)-propenyl)-3,4-dihydroxy-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-3-phenylsulfanyl-(1E)-propenyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-3-phenylsulfanyl-(1Z)-propenyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-3-phenylamino-(1E)-propenyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-3-phenylamino-(1Z)-propenyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-5-(2-Benzylsulfanyl-1-methyl-(1E)-vinyl)-3,4-dihydroxy-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-5-(2-Benzylsulfanyl-1-methyl-(1Z)-vinyl)-3,4-dihydroxy-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-2-phenylmethanesulfonyl-(1E)-vinyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-2-phenylmethanesulfonyl-(1Z)-vinyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-2-phenylsulfamoyl-(1E)-vinyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-2-phenylsulfamoyl-(1Z)-vinyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-5-(2-Fluoro-1-methyl-3-phenoxy-(1E)-propenyl)-3,4-dihydroxy-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-5-(2-Fluoro-1-methyl-3-phenoxy-(1Z)-propenyl)-3,4-dihydroxy-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide.

Each of the above compounds that were made, or can be made, according to the synthetic methods described above fall within the scope of the present invention. Further, the compounds referred to in the table below also fall within the scope of the present invention.

TABLE 1

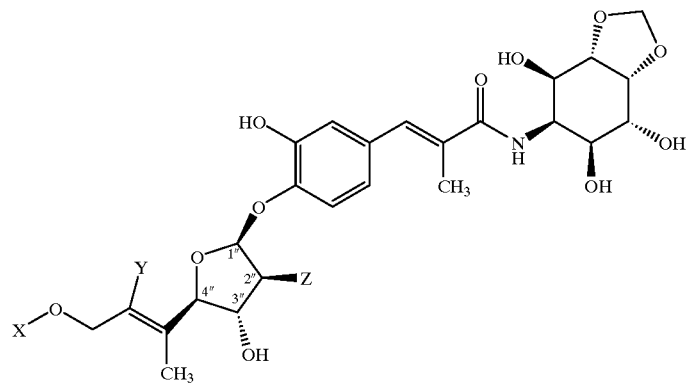

| Ex. | X | Y | Z | Mol Wt | Stereo | Methods | Mass spec. | Representative 1 H NMR peaks (CD₃OD) |
|---|---|---|---|---|---|---|---|---|
| 1 | hydrogen | H | OH | 539.54 | E | A | 540.1 | 5.62 (app. t, J = 6.5 Hz, 1H), 4.17 (m, 2H), 1.56 (s, 3H) |
| 2 | benzyl | H | OH | 629.67 | E | A, D | 630.1 | 7.26 (m, 5H), 5.64 (app. t, J = 6.0 Hz, 1H), 4.38 (s, 2H), 4.28 (m, 2H), 1.55 (s, 3H) |
| 3 | 3-chlorobenzyl | H | OH | 664.11 | E | A, D | 664.0 | 7.25 (m, 3H), 7.16 (m, 1H), 5.64 (app. t, J = 5.9 Hz, 1H), 4.36 (s, 2H), 4.19 (m, 2H), 1.57 (s, 3H) |
| 4 | 2-phenylbenzyl | H | OH | 705.77 | E | A, D | 706.0 | 7.25 (m, 9H), 5.58 (m, 1H), 4.27 (s, 2H), 4.19 (m, 2H), 1.51 (s, 3H) |

TABLE 1-continued

| Ex. | X | Y | Z | Mol Wt | Stereo | Methods | Mass spec. | Representative 1 H NMR peaks (CD₃OD) |
|---|---|---|---|---|---|---|---|---|
| 5 | 4-tert-butylbenzyl | H | OH | 685.78 | E | A, D | 686.2 | 7.30 (d, J = 8.3 Hz, 2H), 7.15 (d, J = 7.1 Hz, 2H), 5.62 (app. t, J = 6.0 Hz, 1H), 4.33 (s, 2H), 4.18 (m, 2H), 1.53 (s, 3H), 1.25 (s, 9H) |
| 6 | 4-fluorobenzyl | H | OH | 647.66 | E | A, D | 648.1 | 7.22 (m, 2H), 6.98 (m, 2H), 5.61 (app. t, J = 6.3 Hz, 1H), 4.33 (s, 2H), 4.19 (m, 2H), 1.53 (s, 3H) |
| 7 | benzoyl | H | OH | 643.65 | E | A, E | 644.2 | 7.91 (d, J = 8.1, 2H), 7.43 (m, 3H), 5.68 (app. t, J = 6.6 Hz, 1H), 4.81 (d, J = 6.6, 2H), 1.70 (s, 3H) |
| 8 | 4-methoxybenzoyl | H | OH | 673.68 | E | A, E | 674.2 | 7.85 (d, J = 9.1, 2H), 6.93 (d, J = 9.1, 2H), 5.66 (app. t, J = 6.5 Hz, 1H), 4.77 (m, 2H), 3.83 (s, 3H), 1.69 (s, 3H) |
| 9 | 2-fluorobenzoyl | H | OH | 661.64 | E | A, E | 662.2 | 7.80 (m, 1H), 7.58 (m, 1H), 7.17 (m, 2H), 5.64 (m, 1H), 4.78 (d, J = 6.6, 2H), 1.70 (s, 3H) |
| 10 | 3-chlorobenzoyl | H | OH | 678.10 | E | A, E | 678.2 | 7.86 (s, 1H), 7.80 (d, J = 7.7 Hz, 1H), 7.56 (d, J = 7.8 Hz, 1H), 7.41 (m, 1H), 5.57 (m, 1H), 4.80 (d, J = 6.8, 2H), 1.68 (s, 3H) |
| 11 | 4-trifluoromethyl-benzoyl | H | OH | 711.65 | E | A, E | 712.2 | 8.07 (d, J = 8.1 2H), 7.73 (d, J = 8.2 Hz, 2H), 5.67 (app. t, J = 6.5 Hz, 1H), 4.82 (d, J = 6.8 Hz, 2H), 1.69 (s, 3H) |
| 12 | benzylcarbamate | H | OH | 672.69 | E | A, F | 673.2 | 7.23 (m, 5H), 5.60 (m, 1H), 4.57 (d, J = 6.2, 2H), 4.23 (s, 2H), 1.61 (s, 3H) |
| 13 | phenylcarbamate | H | OH | 658.67 | E | A, F | 659.2 | 7.43 (m, 2H), 7.24 (m, 2H), 6.98 (m, 1H), 5.65 (app. t, J = 6.0, 1H), 4.64 (m, 2H), 1.66 (s, 3H) |
| 14 | 3-chlorophenyl | H | OH | 650.09 | E | A, G | 650.2 | 7.17 (m, 1H), 6.89 (m, 3H), 5.69 (t, J = 5.7 Hz, 1H), 4.53 (d, J = 6.0 Hz, 2H), 1.66 (s, 3H) |
| 15 | 3-fluorophenyl | H | OH | 633.63 | E | A, G | 634.1 | 7.16 (m, 2H), 6.62 (m, 2H), 5.70 (t, J = |

TABLE 1-continued

| Ex. | X | Y | Z | Mol Wt | Stereo | Methods | Mass spec. | Representative 1 H NMR peaks (CD$_3$OD) |
|---|---|---|---|---|---|---|---|---|
| | | | | | | | | 5.8 Hz, 1H), 4.54 (d, J = 6.2 Hz, 2H), 1.66 (s, 3H) |
| 16 | 3,5-difluorophenyl | H | OH | 651.62 | E | A, G | 652.1 | 7.16 (m, 1H), 6.43 (m, 2H), 5.66 (t, J = 6.1 Hz, 1H), 4.52 (d, J = 6.0 Hz, 2H), 1.64 (s, 1H) |
| 17 | 4-fluorophenyl | H | OH | 633.62 | E | A, G | 634.1 | 6.89 (m, 2H), 6.79 (m, 2H), 5.67 (app. t, J = 6.2 Hz, 1H), 4.48 (d, J = 5.8 Hz, 2H), 1.61 (s, 3H) |
| 18 | 4-chlorophenyl | H | OH | 650.08 | E | A, G | 650.2 | 6.89 (d, J = 9.1 Hz, 2H), 6.75 (d, J = 9.1 Hz, 2H), 5.66 (app. t, J = 5.9 Hz, 1H), 4.49 (d, J = 6.2 Hz, 2H), 1.62 (s, 3H) |
| 19 | 2-chloro-4-fluorophenyl | H | OH | 668.07 | E | A, G | 668.1 | 7.09 (m, 2H), 6.88 (m, 1H), 5.69 (app. t, J = 6.1 Hz, 1H), 4.56 (d, J = 6.2 Hz, 2H), 1.62 (s, 3H) |
| 20 | 3-fluoro-4-chlorophenyl | H | OH | 668.07 | E | A, G | 668.1 | 7.18 (m, 1H), 6.70 (dd, J = 11.2, 2.9 Hz, 1H), 6.61 (ddd, 8.9, 2.7, 1.2 Hz, 1H), 5.65 (app. t, J = 6.1 Hz, 1H), 4.51 (d, J = 6.2 Hz, 2H), 1.64 (s, 1H) |
| 21 | 3,5-dichlorophenyl | H | OH | 684.52 | E | A, G | 582.2 | 6.91 (s, 1H), 6.78 (s, 2H), 5.64 (t, J = 6.1 Hz, 1H), 4.53 (d, J = 6.2 Hz, 2H), 1.64 (s, 1H) |
| 22 | 3-pyridyl | H | OH | 616.62 | E | A, G | 617.2 | 8.02 (m, 1H), 7.59 (m, 1H), 6.88 (m, 1H), 6.68 (d, J = 8.3 Hz, 1H), 5.70 (m, 1H), 4.78 (m, 2H), 1.64 (s, 3H) |
| 23 | 3-chloro-4-fluorophenyl | H | OH | 668.07 | E | A, G | 668.1 | 7.18 (m, 1H), 6.92 (m, 1H), 6.73 (s, 1H), 5.65 (app. t, J = 6.0 Hz, 1H), 4.50 (d, J = 6.2 Hz, 2H), 1.63 (s, 1H) |
| 24 | 3-methoxyphenyl | H | OH | 645.66 | E | A, G | 647.66 | 7.12 (m, 1H), 6.40 (m, 3H), 5.69 (app. t, J = 6.0 Hz, 1H), 4.49 (d, J = 6.4 Hz, 2H), 1.62 (s, 1H) |
| 25 | 2,4-dichlorophenyl | H | OH | 684.53 | E | A, G | 684.2 | 7.12 (m, 2H), 6.85 (d, J = 8.7 Hz, 1H), 5.69 (app. t, J = 6.2 Hz, |

TABLE 1-continued

[Structure diagram of compound with hydroxyl groups, amide, and sugar moiety with X, Y, Z substituents]

| Ex. | X | Y | Z | Mol Wt | Stereo | Methods | Mass spec. | Representative 1 H NMR peaks (CD$_3$OD) |
|---|---|---|---|---|---|---|---|---|
| 26 | 2,4-difluorophenyl | H | OH | 651.62 | E | A, G | 652.2 | 1H), 4.60 (d, J = 6.0 Hz, 2H), 1.66 (s, 3H) 6.91 (m, 2H), 6.78 (m, 1H), 5.70 (app. t, J = 6.2 Hz, 1H), 4.57 (d, J = 6.4 Hz, 2H), 1.63 (s, 3H) |
| 27 | 2-chlorophenyl | H | OH | 650.09 | E | A, G | 650.2 | 7.28 (m, 1H), 7.14 (m, 1H), 6.90 (m, 1H), 6.84 (m, 1H), 5.73 (app. t, J = 6.2 Hz, 1H), 4.60 (d, J = 6.2 Hz, 2H), 1.66 (s, 3H) |
| 28 | 2,6-difluorophenyl | H | OH | 651.62 | E | A, G | 652.1 | 6.97 (m, 1H), 6.88 (m, 2H), 5.72 (app. t, J = 6.8 Hz, 1H), 4.60 (d, J = 7.0 Hz, 2H), 1.56 (s, 3H) |
| 29 | 2-fluorophenyl | H | OH | 633.63 | E | A, G | 634.1 | 6.99 (m, 3H), 6.84 (m, 1H), 5.73 (app. t, J = 6.0 Hz, 1H), 4.60 (d, J = 6.2 Hz, 2H), 1.65 (s, 3H) |
| 30 | 2-propyl-4-fluorophenyl | H | OH | 675.71 | E | A, G | 676.2 | 6.82 (m, 3H), 5.72 (app. t, J = 6.1 Hz, 1H), 4.51 (m, 2H), 2.46 (t, J = 7.5 Hz, 2H), 1.64 (s, 3H), 1.21 (m, 2H), 0.86 (t, J = 7.3 Hz, 3H) |
| 31 | phenyl | H | OH | 615.63 | E | A, G | 616.1 | 7.20 (m, 2H), 6.84 (m, 3H), 5.72 (app. t, J = 5.8 Hz, 1H), 4.53 (d, J = 6.2 Hz, 2H), 1.65 (s, 3H) |
| 32 | 2-benzylphenyl | H | OH | 705.76 | E | A, G | 706.1 | 7.12 (m, 7H), 6.81 (m, 2H), 5.72 (app. t, J = 5.7 Hz, 1H), 4.49 (m, 2H), 3.83 (s, 2H), 1.61 (s,3H) |
| 33 | 2-benzoyl-4-chloro-phenyl | H | OH | 754.18 | E | A, G | 754.0 | 7.66 (d, J = 8.3 Hz, 2H), 7.54 (t, J = 6.2 Hz, 1H), 7.42 (m, 3H), 7.25 (m, 1H), 6.95 (d, J = 8.7 Hz, 1H), 5.40 (app. t, J = 6.2 Hz, 1H), 4.47 (d, J = 6.2 Hz, 2H), 1.48 (s, 3H) |
| 34 | 4-cyanophenyl | H | OH | 640.64 | E | A, G | 641.1 | 7.55 (d, J = 9.1 Hz, 2H), 6.92 (d, J = 8.9 Hz, 2H), 5.67 (app. t, J = 6.0 Hz, 1H), 4.63 (d, J = 6.2 Hz, 2H), 1.68 (s, 3H) |

TABLE 1-continued

| Ex. | X | Y | Z | Mol Wt | Stereo | Methods | Mass spec. | Representative 1 H NMR peaks (CD₃OD) |
|-----|---|---|---|--------|--------|---------|------------|----------------------------------------|
| 35 | 4-indane | H | OH | 655.70 | E | A, G | 656.1 | 6.98 (t, J = 7.6 Hz, 1H), 6.74 (d, J = 7.4 Hz, 1H), 6.57 (d, J = 8.1 Hz, 1H), 5.71 (app. t, J = 6.1 Hz, 1H), 4.53 (d, J = 5.8 Hz, 2H), 1.65 (s, 3H) |
| 36 | 2-fluoro-4-chloro | H | OH | 668.07 | E | A, G | 668.1 | 7.16 (m, 1H), 6.99 (m, 1H), 6.89 (m, 1H), 5.68 (app. t, J = 6.2 Hz, 1H), 4.59 (d, J = 6.4 Hz, 2H), 1.63 (s, 3H) |
| 37 | 2,6-dichlorophenyl | H | OH | 684.52 | E | A, G | 684.1 | 7.28 (d, J = 8.1 Hz, 2H), 7.12 (m, 1H), 5.82 (app. t, J = 6.9 Hz, 1H), 4.56 (m, 2H), 1.61 (s, 3H) |
| 38 | 2-chloro-4-fluoro-phenyl | H | OH | 668.08 | Z | B, G | 668.2 | 7.43 (m, 1H), 7.16 (m, 1H), 6.98 (m, 1H), 5.62 (m, 1H), 4.77 (m, 1H), 4.59 (m, 1H), 1.64 (s, 3H) |
| 39 | 2-chloro-5-fluoro-phenyl | H | OH | 668.07 | E | A, G | 668.0 | 7.26 (dd, J = 8.8, 6.1 Hz, 1H), 6.78 (dd, J = 13.1, 2.5 Hz, 1H), 6.60 (m, 1H), 5.69 (m, 1H), 4.60 (d, J = 6.0 Hz, 2H), 1.66 (s, 3H) |
| 40 | 2,3,4-trichloro-phenyl | H | OH | 718.97 | E | A, G | 717.9 | 7.30 (d, J = 9.0 Hz, 1H), 6.83 (d, J = 8.9 Hz, 1H), 5.66 (m, 1H), 4.66 (d, J = 6.1 Hz, 2H), 1.67 (s, 3H) |
| 41 | 2,3-dichlorophenyl | H | OH | 684.53 | E | A, G | 684.0 | 7.23 (m, 1H), 7.02 (d, J = 8.0 Hz, 1H), 6.85 (m, 1H), 5.70 (t, J = 6.1 Hz, 1H), 4.63 (d, J = 6.3 Hz, 2H), 1.66 (s, 3H) |
| 42 | 2,5-dichlorophenyl | H | OH | 684.53 | E | B, G | 684.1 | 7.26 (d, J = 8.5 Hz, 1H), 6.98 (d, J = 2.2 Hz, 1H), 6.84 (m, 1H), 5.69 (t, J = 5.7, 1H), 4.62 (d, J = 6.1 Hz, 2H), 1.68 (s, 3H) |
| 43 | 2,5-dichlorophenyl | H | OH | 684.53 | Z | B, G | 684.1 | 7.30 (d, J = 8.5 Hz, 1H), 7.05 (d, J = 2.3 Hz, 1H), 6.90 (m, 1H), 5.65 (t, J = 5.8, 1H), 4.82 (m, 1H), 4.61 (m, 1H), 1.66 (s, 3H) |
| 44 | 2-chlorophenyl | H | OH | 650.09 | Z | B, G | 650.1 | 7.29 (dd, J = 8.0, 1.4 Hz, 1H), 7.14 (m, 1H), 6.94 (d, J = 7.2 Hz, 1H), 6.84 (m, |

TABLE 1-continued

| Ex. | X | Y | Z | Mol Wt | Stereo | Methods | Mass spec. | Representative 1 H NMR peaks (CD₃OD) |
|---|---|---|---|---|---|---|---|---|
| | | | | | | | | 1H), 5.64 (m, 1H), 4.80 (m, 1H), 4.58 (m, 1H), 1.63 (s, 3H) |
| 45 | 2-fluorophenyl | H | OH | 633.63 | Z | B, G | 634.1 | 6.99 (m, 3H), 6.84 (m, 1H), 5.64 (m, 1H), 4.80 (m, 1H), 4.56 (m, 1H), 1.62 (s, 3H) |
| 46 | 2,4-dichlorophenyl | H | OH | 684.53 | Z | B, G | 684.0 | 7.34 (d, J = 2.5 Hz, 1H), 7.15 (m, 1H), 6.93 (d, J = 8.7 Hz, 1H), 5.61 (m, 1H), 4.78 (m, 1H), 4.59 (m, 1H), 1.63 (s, 3H) |
| 47 | 2-chloro-5-fluoro-phenyl | H | OH | 668.07 | Z | B, G | 668.1 | 7.30 (dd, J = 8.7, 6.0 Hz, 1H), 6.83 (m, 1H), 6.62 (m, 1H), 5.62 (m, 1H), 4.78 (m, 1H), 4.59 (m, 1H), 1.64 (s, 3H) |
| 48 | 2-chloro-3,5-difluoro-phenyl | H | OH | 686.06 | E | B, G | 686.1 | 6.66 (s, 1H), 6.63 (s, 2H), 5.69 (t, J = 5.8 Hz, 1H), 4.66 (d, J = 6.0 Hz, 2H), 1.69 (s, 3H) |
| 49 | 2-chloro-3,5-difluoro-phenyl | H | OH | 686.06 | Z | B, G | 686.1 | 6.69 (m, 2H), 5.63 (t, J = 6.3 Hz, 1H), 4.78 (m, 1H), 4.61 (m, 1H), 1.64 (s, 3H) |
| 50 | 2,4,5-trichlorophenyl | H | OH | 718.98 | Z | B, G | 718.0 | 7.50 (s, 1H), 7.17 (s, 1H), 5.62 (app. t, J = 5.9 Hz, 1H), 4.77 (m, 1H), 4.59 (dd, J = 11.2, 4.6 Hz, 1H), 1.64 (s, 3H) |
| 51 | 2,4,5-trichlorophenyl | H | OH | 718.98 | E | B, G | 718.0 | 7.44 (s, 1H), 7.12 (s, 1H), 5.65 (app. t, J = 6.0 Hz, 1H), 4.60 (d, J = 6.2 Hz, 2H), 1.66 (s, 3H) |
| 52 | 2-trifluoromethyl-4-fluorophenyl | H | OH | 701.62 | Z | B, G | 702.1 | 7.29 (s, 2H)7. 7.18 (m, 1H), 7.06 (dd, J = 9.3, 4.1 Hz, 1H), 5.57 (m, 1H), 4.77 (m, 1H), 4.62 (m, 1H), 1.62 (s, 3H) |
| 53 | 2-trifluoromethyl-4-fluorophenyl | H | OH | 701.62 | E | B, G | 702.1 | 7.25 (dd, J = 8.7, 3.1 Hz, 1H), 7.17 (m, 1H), 7.00 (dd J = 9.2, 4.2 Hz, 1H), 5.67 (app. t, J = 5.8 Hz, 1H), 4.64 (d, J = 6.0 Hz, 2H), 1.65 (s, 3H) |
| 54 | 2-trifluoromethyl-phenyl | H | OH | 683.63 | Z | B, G | 684.1 | 7.50 (d, J = 7.9 Hz, 1H), 7.47 (app. t, J = 8.0 Hz, 1H), 7.03 (d, J = 8.3 Hz, 1H), 6.99 |

TABLE 1-continued

| Ex. | X | Y | Z | Mol Wt | Stereo | Methods | Mass spec. | Representative 1 H NMR peaks (CD₃OD) |
|---|---|---|---|---|---|---|---|---|
| 55 | 2-trifluoromethyl-phenyl | H | OH | 683.63 | E | B, G | 684.1 | (app. t, 7.7 Hz, 1H), 5.59 (m, 1H), 4.74 (m, 1H), 4.63 (m, 1H), 1.63 (s, 3H) 7.48 (d, J = 7.9 Hz, 1H), 7.45 (app. t, J = 8.0 Hz, 1H), 6.99 (d, J = 8.8 Hz, 1H), 6.96 (app. t, 7.7 Hz, 1H), 5.70 (app. t, J = 6.1 Hz, 1H), 4.65 (d, J = 6.0 Hz, 2H), 1.66 (s, 3H) |
| 56 | 2-chloro-4-fluoro-phenyl | Me | OH | 682.10 | Z | C, G | 682.1 | 7.17 (m, 1H), 7.06 (m, 1H), 6.98 (m, 1H), 4.89 (m, 1H), 4.49 (m, 1H), 1.81 (s, 3H), 1.60 (s, 3H) |
| 57 | 2-chlorophenyl | Me | OH | 664.11 | Z | C, G | 664.1 | 7.44 (d, J = 8.9 Hz, 1H), 7.32 (dd J = 7.9, 1.4 Hz, 1H), 7.05 (d, J = 8.1 Hz, 1H), 6.87 (m, 1H), 4.90 (m, 1H), 4.48 (m, 1H), 1.82 (s, 3H), 1.61 (s, 3H) |
| 58 | 2-chloro-4-fluoro-phenyl | H | H | 652.08 | Z | J, G | 652.0 | 7.14 (m, 1H), 6.91 (m, 2H), 5.62 (m, 1H), 4.77 (m, 1H), 4.56 (m, 1H), 1.66 (s, 3H) |
| 59 | 2-chloro-4-fluoro-phenyl | H | H | 652.08 | E | J, G | 652.0 | 7.12 (m, 1H), 6.92 (m, 2H), 5.76 (app. t, J = 6.1 Hz, 1H), 4.55 (d, J = 6.2 Hz, 2H), 1.67 (s, 3H) |
| 60 | 2,3-dichloro-phenyl | H | H | 668.53 | E | I, G | 668.0 | 7.15 (m, 1H), 7.04 (d, J = 8.3 Hz, 1H), 6.88 (m, 1H), 5.77 (app. t, J = 6.1 Hz, 1H), 4.65 (d, J = 6.2 Hz, 2H), 1.70 (s, 3H) |
| 61 | 2,3,4-trichloro-phenyl | H | H | 702.98 | E | I, G | 702.0 | 7.30 (d, J = 9.1 Hz, 1H), 6.88 (m, 1H), 5.74 (app. t, J = 6.0 Hz, 1H), 4.66 (d, J = 6.0 Hz, 2H), 1.70 (s, 3H) |
| 62 | 2,4,5-trichloro-phenyl | H | H | 702.98 | E | I, G | 702.0 | 7.47 (s, 1H), 7.10 (s, 1H), 5.74 (app. t, J = 6.6 Hz, 1H), 4.65 (d, J = 6.0 Hz, 2H), 1.70 (s, 3H) |
| 63 | 2,5-dichloro-phenyl | H | H | 668.53 | E | I, G | 668.0 | 7.24 (d, J = 8.5 Hz, 1H), 6.98 (d, J = 2.2 Hz, 1H), 6.84 (m, 1H), 5.78 (app. t, J = |

TABLE 1-continued

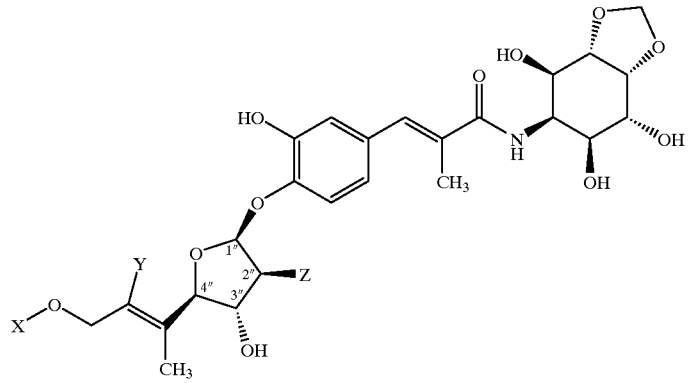

| Ex. | X | Y | Z | Mol Wt | Stereo | Methods | Mass spec. | Representative 1 H NMR peaks (CD₃OD) |
|---|---|---|---|---|---|---|---|---|
| 64 | 3-chlorophenyl | H | H | 634.09 | E | I, G | 634.0 | 6.8, 1H), 4.62 (d, J = 6.3 Hz, 2H), 1.69 (s, 3H) 7.17 (m, 1H), 6.89 (m, 2H), 6.76 (m, 1H), 5.74 (app. t, J = 5.1 Hz, 1H), 4.53 (d, J = 6.2 Hz, 2H), 1.67 (s, 3H) |
| 65 | 3-fluorophenyl | H | H | 617.23 | E | I, G | 618.1 | 7.16 (m, 1H), 6.62 (m, 3H), 5.74 (m, 1H), 4.53 (d, J = 6.5 Hz, 2H), 1.67 (s, 3H) |
| 66 | 2,4-difluorophenyl | H | H | 635.62 | E | I, G | 636.1 | 6.92 (m, 2H), 6.76 (m, 1H), 5.75 (m, 1H), 4.57 (d, J = 6.5 Hz, 2H), 1.63 (s, 3H) |
| 67 | 2-chlorophenyl | H | H | 634.09 | E | I, G | 634.0 | 7.29 (m, 1H), 7.14 (m, 1H), 6.95 (m, 1H), 6.82 (m, 1H), 5.82 (app. t, J = 6.4 Hz, 1H), 4.64 (d, J = 6.0 Hz, 2H), 1.70 (s, 3H) |
| 68 | 2,4-dichlorophenyl | H | H | 668.53 | E | I, G | 668.0 | 7.32 (m, 1H), 7.14 (m, 1H), 6.91 (d J = 8.9 Hz, 1H), 5.78 (app. t, J = 5.9 Hz, 1H), 4.64 (d, J = 6.2 Hz, 2H), 1.71 (s, 3H) |
| 69 | 2-chloro-5-fluorophenyl | H | H | 652.08 | E | I, G | 652.0 | 7.28 (dd, J = 8.6, 6.2 Hz, 1H), 6.79 (m, 1H), 6.61 (m, 1H), 5.76 (m, 1H), 4.62 (d, J = 6.2 Hz, 2H), 1.70 (s, 3H) |
| 70 | 2-chloro-3,5-difluorophenyl | H | H | 670.07 | E | I, G | 670.0 | 6.64 (m, 2H), 5.76 (m t, 1H), 4.65 (d, J = 6.2 Hz, 2H), 1.71 (s, 3H) |
| 71 | 3,5-difluorophenyl | H | H | 635.62 | E | I, G | 636.1 | 7.18 (m, 1H), 6.45 (m, 2H), 5.74 (m, 1H), 4.56 (d, J = 6.3 Hz, 2H), 1.70 (s, 1H) |
| 72 | 3-fluoro-4-chlorophenyl | H | H | 652.08 | E | I, G | 652.1 | 7.18 (m, 1H), 6.76 (dd, J = 11.2, 2.7 Hz, 1H), 6.67 (m, 1H), 5.74 (app. t, J = 6.0 Hz, 1H), 4.56 (d J = 6.2 Hz, 2H), 1.70 (s, 1H) |
| 73 | 2-fluoro-4-chlorophenyl | H | H | 652.08 | E | I, G | 652.1 | 7.14 (m, 1H), 7.02 (m, 1H), 6.96 (m, 1H), 5.77 (app. t, J = 6.3 Hz, 1H), 4.63 (d, J = 6.4 Hz, 2H), 1.69 (s, 3H) |

What is claimed is:
1. A compound of the formula

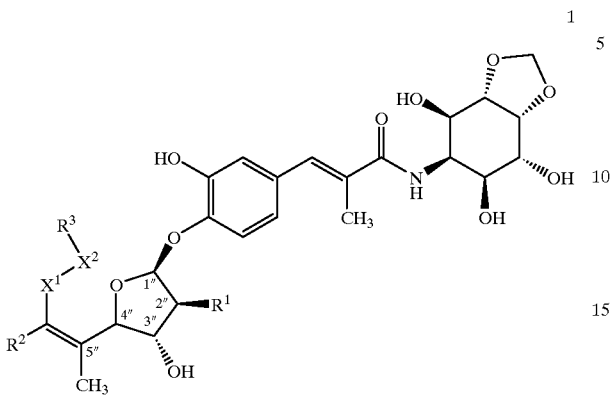

or a pharmaceutically acceptable salt or solvate thereof wherein:

$X^1$ and $X^2$ are each independently selected from the group consisting of —$CR^6R^7$—, —$S(O)_n$— wherein n is 0 to 2, —$NR^6$—, and O, except that (a) if either $X^1$ or $X^2$ is O, S, or S(O) then the other moiety ($X^1$ or $X^2$) is —$CR^6R^7$—; (b) if either $X^1$ or $X^2$ is $SO_2$ then the other moiety ($X^1$ or $X^2$) is —$NR^6$— or —$CR^6R^7$—; and (c) if $X^1$ is —$NR^6$—, then $X^2$ is $SO_2$ or —C(O)—;

$R^1$ is H or OH;

$R^2$ is H, $C_1$–$C_6$ alkyl, or halo, wherein the foregoing $R^2$ alkyl group is optionally substituted by 1 or 2 $R^4$ groups;

or where $X^2$ is —$NR^6$—, then $R^3$ and $X^2$ may be taken together to form a 5 to 12 membered ring, wherein said ring is saturated or partially unsaturated with up to 3 carbon-carbon double bonds, the carbon atoms of said ring are optionally subsituted by 1 to 3 $R^4$ groups, and the ring optionally contains up to 2 additional hetero moieties (in addition to the $X^2$ moiety which is —$NR^6$—) selected from O, $S(O)_j$ wherein j is an integer from 0 to 2, and —$NR^6$—, with the proviso that two O atoms, two S atoms, an O and S atom, an N and O atom, and an N and S atom are not attached directly to each other;

each $R^3$ is independently selected from the group consisting of H, $C_1$–$C_{10}$ alkyl, —$(CR^6R^7)_t(C_6$–$C_{10}$ aryl), —$(CR^6R^7)_t$(4–10 membered heterocyclic), —C(O)$(CR^6R^7)_t(C_6$–$C_{10}$ aryl), —C(O)$(CR^6R^7)_t$(4–10 membered heterocyclic), —C(O)$NR^6(CR^6R^7)_t(C_6$–$C_{10}$ aryl), and —C(O)$NR^6(CR^6R^7)_t$(4–10 membered heterocyclic), wherein t is an integer ranging from 0 to 5, said alkyl group optionally contains 1 or 2 hetero moieties selected from O, —$S(O)_j$— wherein j is an integer ranging from 0 to 2, and —$NR^6$— with the proviso that two O atoms, two S atoms, an O and S atom, an N and O atom, and an N and S atom are not attached directly to each other; the —$(CR^6R^7)_t$— moieties of the foregoing $R^3$ groups optionally include a carbon-carbon double or triple bond where t is an integer between 2 and 5; and the heterocyclic and aryl moieties of the foregoing $R^3$ groups are optionally substituted by 1 to 5 $R^4$ groups;

each $R^4$ is independently selected from the group consisting of $C_1$–$C_{10}$ alkyl, $C_2$–$C_{10}$ alkenyl, $C_2$–$C_{10}$ alkynyl, halo, cyano, nitro, trifluoromethyl, trifluoromethoxy, azido, hydroxy, $C_1$–$C_6$ alkoxy, —C(O)$R^5$, —C(O)O$R^5$, —$NR^6$C(O)O$R^8$, —OC(O)$R^5$, —$NR^6SO_2R^8$, —$SO_2NR^5R^6$, —$NR^6C(O)R^5$, —C(O) $NR^5R^6$, —$NR^5R^6$, —$S(O)_j(CR^6R^7)_m(C_6$–$C_{10}$ aryl), —$S(O)_j(C_1$–$C_6$ alkyl), —$(CR^6R^7)_m(C_6$–$C_{10}$ aryl), —O$(CR^6R^7)_m(C_6$–$C_{10}$ aryl), —$NR^6(CR^6R^7)_m(C_6$–$C_{10}$ aryl), —$(CR^6R^7)_m$(4–10 membered heterocyclic), —C(O)$(CR^6R^7)_m(C_6$–$C_{10}$ aryl), and —C(O)$(CR^6R^7)_m$ (4–10 membered heterocyclic), wherein m is an integer from 0 to 4; j is an integer from 0 to 2, and said alkyl, alkenyl, alkynyl, aryl and heterocyclic moieties of the foregoing $R^4$ groups are optionally substituted by 1 to 3 substituents independently selected from the group consisting of halo, cyano, nitro, trifluoromethyl, trifluoromethoxy, azido, —$NR^6SO_2R^8$, —$SO_2NR^5R^6$, —C(O)$R^5$, —C(O)O$R^5$, —OC(O)$R^5$, —$NR^6C(O)OR^8$, —$NR^6C(O)R^5$, —C(O)$NR^5R^6$, —$NR^5R^6$, —O$R^5$, $C_1$–$C_{10}$ alkyl, —$(CR^6R^7)_m(C_6$–$C_{10}$ aryl), and —$(CR^6R^7)_m$(4–10 membered heterocyclic), wherein m is an integer from 0 to 4;

each $R^5$ is independently selected from the group consisting of H, $C_1$–$C_{10}$ alkyl, —$(CR^6R^7)_m(C_6$–$C_{10}$ aryl), and —$(CR^6R^7)_m$(4–10 membered heterocyclic), wherein m is an integer from 0 to 4, and the foregoing $R^5$ substituents, except H, are optionally substituted by 1 to 3 substituents independently selected from the group consisting of halo, cyano, nitro, trifluoromethyl, trifluoromethoxy, azido, —C(O)$R^6$, —C(O)O$R^6$, —OC(O)$R^6$, —$NR^6C(O)R^7$, —C(O)$NR^6R^7$, —$NR^6R^7$, hydroxy, $C_1$–$C_6$ alkyl, and $C_1$–$C_6$ alkoxy;

each $R^6$ and $R^7$ is independently H, —C(O)($C_1$–$C_6$ alkyl), $C_1$–$C_6$ alkyl or fluoro; and, $R^8$ is selected from the substituents provided in the definition of $R^5$ except $R^8$ is not H.

2. A compound according to claim 1 wherein $X^1$ is —$CH_2$— and $X^2$ is O.

3. A compound according to claim 1 wherein $X^1$ is —$CH_2$—, $X^2$ is O, and $R^3$ is —$(CR^6R^7)_t(C_6$–$C_{10}$ aryl) wherein t is as defined in claim 1, $R^6$ and $R^7$ are both H, and said aryl group is optionally substituted by 1 to 5 $R^4$ groups.

4. A compound according to claim 3 wherein said aryl group is a phenyl group optionally substituted by 1 to 5 $R^4$ groups.

5. A compound according to claim 1 wherein $X^1$ is —$CH_2$—, $X^2$ is O, and $R^3$ is —$(CR^6R^7)_t$(4–10 membered heterocyclic), wherein t is as defined in claim 1, $R^6$ and $R^7$ are both H, and said heterocyclic group is optionally substituted by 1 to 4 $R^4$ groups.

6. A compound according to claim 5 wherein said heterocyclic group is a pyridyl group or benzothiazolyl group optionally substituted by 1 to 4 $R^4$ groups.

7. A compound according to claim 1 wherein $X^1$ is —$CH_2$—, $X^2$ is O, and $R^3$ is —C(O)$(CR^6R^7)_t(C_6$–$C_{10}$ aryl) wherein t is as defined in claim 1, $R^6$ and $R^7$ are both H, and said aryl group is optionally substituted by 1 to 4 $R^4$ groups.

8. A compound according to claim 7 wherein said aryl group is a phenyl group optionally substituted by 1 to 4 $R^4$ groups.

9. A compound according to claim 1 wherein $X^1$ is —$CH_2$—, $X^2$ is O, and $R^3$ is —C(O)$NR^6(CR^6R^7)_t(C_6$–$C_{10}$ aryl) wherein t is as defined in claim 1, $R^6$ and $R^7$ are both H, and said aryl group is optionally substituted by 1 to 4 $R^4$ groups.

10. A compound according to claim 9 wherein said aryl group is a phenyl group optionally substituted by 1 to 4 $R^4$ groups.

11. A compound according to claim 1 wherein said compound is selected from the group consisting of:

3-(4-((2S,3S,4S,5R)-3,4-Dihydroxy-5-(3-hydroxy-1-methyl-(1E)-propenyl)-tetrahydro-furan-2-yloxy)-3-hydroxy-phenyl)-2-methyl-N-((3aS,4R,5R,6S,7R,7aR)-4,6,7-trihydroxy-benzo(1,3)dioxol-5-yl)-(2E)-acrylamide;

3-(4-((2S,3S,4S,5R)5-(3-Benzyloxy-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-benzo(1,3)dioxol-5-yl)-(2E)-acrylamide;

3-(4-((2S,3S,4S,5R)5-(3-(3-Chloro-benzyloxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-benzo(1,3)dioxol-5-yl)-(2E)-acrylamide;

3-(4-((2S,3S,4S,5R)5-(3-(Biphenyl-2-ylmethoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-benzo(1,3)dioxol-5-yl)-(2E)-acrylamide;

3-(4-((2S,3S,4S,5R)5-(3-(4-tert-Butyl-benzyloxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-benzo(1,3)dioxol-5-yl)-(2E)-acrylamide;

3-(4-((2S,3S,4S,5R)5-(3-(4-Fluoro-benzyloxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-benzo(1,3)dioxol-5-yl)-(2E)-acrylamide;

Benzoic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

4-Methoxy-benzoic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

2-Fluoro-benzoic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

3-Chloro-benzoic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

4-Trifluoromethyl-benzoic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

Benzyl-carbamic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

Phenyl-carbamic acid 3-((2S,3S,4S,5R)-3,4-dihydroxy-5-(2-hydroxy-4-(2-((3aS,4R,5R,6S,7R,7aR)-4,6,7-trihydroxy-hexahydro-benzo(1,3)dioxol-5-ylcarbamoyl)-(1E)-propenyl)-phenoxy)-tetrahydro-furan-2-yl)-(2E)-but-2-enyl ester;

3-(4-((2S,3S,4S,5R)-5-(3-(3-Chloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3-Fluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3,5-Difluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Fluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Chloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-4-fluro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Chloro-3-fluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3,5-Dichloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3-chloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(pyridin-3-yloxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3-chloro-4-fluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(3-Methoxy-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,4-Dichloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,4-Difluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-chloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,6-Difluoro-phenoxy)-1-methyl-(1E)-propenyl)-3,4-dihydroxy-tetrahydrofuran-2-yloxy)-3-hydroxy-phenyl)-2-methyl-N-((3aS, 4R,5R,6S,7R,7aR)-4,6,7-trihydroxy-hexahydro-benzo (1,3)dioxol-5-yl)-(2E)-acrylamide;

3-(4-((2S,3S,4S,5R)-5-(3-(3-chloro-phenoxy)-1-methyl-(1E)-propenyl)-3,4-dihydroxy-tetrahydro-furan-2-yloxy)-3-hydroxy-phenyl)-2-methyl-N-((3aS,4R,5R, 6S,7R,7aR)-4,6,7-trihydroxy-hexahydro-benzo(1,3)dioxol-5-yl)-(2E)-acrylamide;

3-(4-((2S,3S,4S,5R)-5-(3-(2-Fluoro-phenoxy)-1-methyl-(1E)-propenyl)-3,4-dihydroxy-tetrahydro-furan-2-yloxy)-3-hydroxy-phenyl)-2-methyl-N-((3aS,4R,5R, 6S,7R,7aR)-4,6,7-trihydroxy-hexahydro-benzo(1,3)dioxol-5-yl)-(2E)-acrylamide;

3-(4-((2S,3S,4S,5R)-5-(3-(4-Fluoro-2-propyl-phenoxy)-1-methyl-(1E)-propenyl)-3,4-dihydroxy-tetrahydro-furan-2-yloxy)-3-hydroxy-phenyl)-2-methyl-N-((3aS, 4R,5R,6S,7R,7aR)-4,6,7-trihydroxy-hexahydro-benzo (1,3)dioxol-5-yl)-(2E)-acrylamide;

3-(4-((2S,3S,4S,5R)-5-(3-phenoxy-1-methyl-(1E)-propenyl)-3,4-dihydroxy-tetrahydro-furan-2-yloxy)-3-hydroxy-phenyl)-2-methyl-N-((3aS,4R,5R,6S,7R, 7aR)-4,6,7-trihydroxy-hexahydro-benzo(1,3)dioxol-5-yl)-(2E)-acrylamide;

3-(4-((2S,3S,4S,5R)-5-(3-(2-Benzyl-phenoxy)-1-methyl-(1E)-propenyl)-3,4-dihydroxy-tetrahydro-furan-2-yloxy)-3-hydroxy-phenyl)-2-methyl-N-((3aS,4R,5R, 6S,7R,7aR)-4,6,7-trihydroxy-hexahydro-benzo(1,3)dioxol-5-yl)-(2E)-acrylamide;

3-(4-((2S,3S,4S,5R)-5-(3-(2-Benzoyl-4-chloro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Cyano-phenoxy)-1-methyl-(1E)-propenyl)-3,4-dihydroxy-tetrahydro-furan-2-yloxy)-3-hydroxy-phenyl)-2-methyl-N-((3aS,4R,5R, 6S,7R,7aR)-4,6,7-trihydroxy-hexahydro-benzo(1,3)dioxol-5-yl)-(2E)-acrylamide;

3-(4-((2S,3S,4S,5R)-5-(3-(Indan-4-yloxy)-1-methyl-(1E)-propenyl)-3,4-dihydroxy-tetrahydro-furan-2-yloxy)-3-hydroxy-phenyl)-2-methyl-N-((3aS,4R,5R, 6S,7R,7aR)-4,6,7-trihydroxy-hexahydro-benzo(1,3)dioxol-5-yl)-(2E)-acrylamide;

3-(4-((2S,3S,4S,5R)-5-(3-(4-Chloro-2-fluoro-phenoxy)-1-methyl-(1E)-propenyl)-3,4-dihydroxy-tetrahydro-furan-2-yloxy)-3-hydroxy-phenyl)-2-methyl-N-((3aS, 4R,5R,6S,7R,7aR)-4,6,7-trihydroxy-hexahydro-benzo (1,3)dioxol-5-yl)-(2E)-acrylamide;

3-(4-((2S,3S,4S,5R)-5-(3-(2,6-Dichloro-phenoxy)-1-methyl-(1E)-propenyl)-3,4-dihydroxy-tetrahydro-furan-2-yloxy)-3-hydroxy-phenyl)-2-methyl-N-((3aS, 4R,5R,6S,7R,7aR)-4,6,7-trihydroxy-hexahydro-benzo (1,3)dioxol-5-yl)-(2E)-acrylamide;

3-(4-((2S,3S,4S,5R)-5-(3-(2-Chloro-4-fluoro-phenoxy)-1-methyl-(1Z)-propenyl)-3,4-dihydroxy-tetrahydro-furan-2-yloxy)-3-hydroxy-phenyl)-2-methyl-N-((3aS, 4R,5R,6S,7R,7aR)-4,6,7-trihydroxy-hexahydro-benzo (1,3)dioxol-5-yl)-(2E)-acrylamide;

3-(4-((2S,3S,4S,5R)-5-(3-(2-Chloro-5-fluoro-phenoxy)-1-methyl-(1E)-propenyl)-3,4-dihydroxy-tetrahydro-furan-2-yloxy)-3-hydroxy-phenyl)-2-methyl-N-((3aS, 4R,5R,6S,7R,7aR)-4,6,7-trihydroxy-hexahydro-benzo (1,3)dioxol-5-yl)-(2E)-acrylamide;

3-(4-((2S,3S,4S,5R)-5-(3-(2,3,4-Trichloro-phenoxy)-1-methyl-(1E)-propenyl)-3,4-dihydroxy-tetrahydro-furan-2-yloxy)-3-hydroxy-phenyl)-2-methyl-N-((3aS, 4R,5R,6S,7R,7aR)-4,6,7-trihydroxy-hexahydro-benzo (1,3)dioxol-5-yl)-(2E)-acrylamide;

3-(4-((2S,3S,4S,5R)-5-(3-(2,3-Dichloro-phenoxy)-1-methyl-(1E)-propenyl)-3,4-dihydroxy-tetrahydro-furan-2-yloxy)-3-hydroxy-phenyl)-2-methyl-N-((3aS, 4R,5R,6S,7R,7aR)-4,6,7-trihydroxy-hexahydro-benzo (1,3)dioxol-5-yl)-(2E)-acrylamide;

3-(4-((2S,3S,4S,5R)-5-(3-(2,5-Dichloro-phenoxy)-1-methyl-(1E)-propenyl)-3,4-dihydroxy-tetrahydro-furan-2-yloxy)-3-hydroxy-phenyl)-2-methyl-N-((3aS, 4R,5R,6S,7R,7aR)-4,6,7-trihydroxy-hexahydro-benzo (1,3)dioxol-5-yl)-(2E)-acrylamide;

3-(4-((2S,3S,4S,5R)-5-(3-(2,5-Dichloro-phenoxy)-1-methyl-(1Z)-propenyl)-3,4-dihydroxy-tetrahydro-furan-2-yloxy)-3-hydroxy-phenyl)-2-methyl-N-((3aS, 4R,5R,6S,7R,7aR)-4,6,7-trihydroxy-hexahydro-benzo (1,3)dioxol-5-yl)-(2E)-acrylamide;

3-(4-((2S,3S,4S,5R)-5-(3-(2-Chloro-phenoxy)-1-methyl-(1Z)-propenyl)-3,4-dihydroxy-tetrahydro-furan-2-yloxy)-3-hydroxy-phenyl)-2-methyl-N-((3aS,4R,5R, 6S,7R,7aR)-4,6,7-trihydroxy-hexahydro-benzo(1,3)dioxol-5-yl)-(2E)-acrylamide;

3-(4-((2S,3S,4S,5R)-5-(3-(2-Fluoro-phenoxy)-1-methyl-(1Z)-propenyl)-3,4-dihydroxy-tetrahydro-furan-2-yloxy)-3-hydroxy-phenyl)-2-methyl-N-((3aS,4R,5R, 6S,7R,7aR)-4,6,7-trihydroxy-hexahydro-benzo(1,3)dioxol-5-yl)-(2E)-acrylamide;

3-(4-((2S,3S,4S,5R)-5-(3-(2,4-Dichloro-phenoxy)-1-methyl-(1Z)-propenyl)-3,4-dihydroxy-tetrahydro-furan-2-yloxy)-3-hydroxy-phenyl)-2-methyl-N-((3aS, 4R,5R,6S,7R,7aR)-4,6,7-trihydroxy-hexahydro-benzo (1,3)dioxol-5-yl)-(2E)-acrylamide;

3-(4-((2S,3S,4S,5R)-5-(3-(2-Chloro-5-fluoro-phenoxy)-1-methyl-(1Z)-propenyl)-3,4-dihydroxy-tetrahydro-furan-2-yloxy)-3-hydroxy-phenyl)-2-methyl-N-((3aS, 4R,5R,6S,7R,7aR)-4,6,7-trihydroxy-hexahydro-benzo (1,3)dioxol-5-yl)-(2E)-acrylamide;

3-(4-((2S,3S,4S,5R)-5-(3-(2-Chloro-3,5-difluoro-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-3,5-difluoro-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2,4,5-Trichloro-phenoxy)-1-methyl-(1Z)-propenyl)-3,4-dihydroxy-tetrahydro-furan-2-yloxy)-3-hydroxy-phenyl)-2-methyl-N-((3aS, 4R,5R,6S,7R,7aR)-4,6,7-trihydroxy-hexahydro-benzo (1,3)dioxol-5-yl)-(2E)-acrylamide;

3-(4-((2S,3S,4S,5R)-5-(3-(2,4,5-Trichloro-phenoxy)-1-methyl-(1E)-propenyl)-3,4-dihydroxy-tetrahydro-furan-2-yloxy)-3-hydroxy-phenyl)-2-methyl-N-((3aS, 4R,5R,6S,7R,7aR)-4,6,7-trihydroxy-hexahydro-benzo (1,3)dioxol-5-yl)-(2E)-acrylamide;

3-(4-((2S,3S,4S,5R)-5-(3-(4-Fluoro-2-trifluoromethyl-phenoxy)-1-methyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(4-Fluoro-2-trifluoromethyl-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Trifluoromethyl-phenoxy)-1-methyl-(1Z)-propenyl)-3,4-dihydroxy-tetrahydro-furan-2-yloxy)-3-hydroxy-phenyl)-2-methyl-N-((3aS, 4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Trifluoromethyl-phenoxy)-1-methyl-(1E)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-4-fluoro-phenoxy)-1,2-dimethyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,3S,4S,5R)-5-(3-(2-Chloro-phenoxy)-1,2-dimethyl-(1Z)-propenyl)-3,4-dihydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2-Chloro-4-fluoro-phenoxy)-1-methyl-(1Z)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2-Chloro-4-fluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,3-Dichloro-4-fluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,3,4-trichloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,4,5-trichloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,5-Dichloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(3-Chloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(3-Fluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,4-Difluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2-Chloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2,4-Dichloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2-Chloro-5-fluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2-Chloro-3,5-difluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(3,5-Difluoro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(3-Fluoro-4-chloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide;

3-(4-((2S,4S,5R)-5-(3-(2-Fluoro-4-chloro-phenoxy)-1-methyl-(1E)-propenyl)-4-hydroxy-tetrahydro-furan-2-yloxy)-3-hydroxy-phenyl)-2-methyl-N-((3aS,4R,5R,6S,7R,7aR)-4,6,7-trihydroxy-hexahydro-benzo(1,3)dioxol-5-yl)-(2E)-acrylamide; and the pharmaceutically acceptable salts of the foregoing compounds.

12. A compound according to claim 1 wherein said compound is selected from the group consisting of:

3-(4-{(2S,3S,4S,5R)-5-[3-(Benzothiazol-6-yloxy)-1-methyl-(1E)-propenyl]-3,4-dihydroxy-tetrahydro-furan-2-yloxy}-3-hydroxy-phenyl)-2-methyl-N- ((3aS,4R,5R,6S,7R,7aR)-4,6,7-trihydroxy-hexahydro-benzo[1,3]dioxol-5-yl)-acrylamide;

3-(4-{(2S,3S,4S,5R)-5-[3-(Benzothiazol-6-yloxy)-1-methyl-(1Z)-propenyl]-3,4-dihydroxy-tetrahydro-furan-2-yloxy}-3-hydroxy-phenyl)-2-methyl-N- ((3aS,4R,5R,6S,7R,7aR)-4,6,7-trihydroxy-hexahydro-benzo[1,3]dioxol-5-yl)-acrylamide;

3-(4-{(2S,3S,4S,5R)-5-[3-(2-Chloro-pyridin-3-yloxy)-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-acrylamide;

3-(4-{(2S,3S,4S,5R)-5-[3-(2-Chloro-pyridin-3-yloxy)-1-methyl-(1Z)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-acrylamide;

3-[4-((2S,3S,4S,5R)-5-{3-[2,4-Dichloro-6-(methoxyimino-methyl)-phenoxy]-1-methyl-(1E)-propenyl}-3,4-dihydroxy-tetrahydro-furan-2-yloxy)-3-hydroxy-phenyl]-2-methyl-N-((3aS,4R,5R,6S,7R,7aR)-4,6,7-trihydroxy-hexahydro-benzo[1,3]dioxol-5-yl)-(2E)-acrylamide;

3-[4-((2S,3S,4S,5R)-5-{3-[2,4-Dichloro-6-(methoxyimino-methyl)-phenoxy]-1-methyl-(1Z)-propenyl}-3,4-dihydroxy-tetrahydro-furan-2-yloxy)-3-hydroxy-phenyl]-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-(2-Acetyl-4,6-dichloro-phenoxy)-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-(2-Acetyl-4,6-dichloro-phenoxy)-1-methyl-(1Z)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-3,4-Dihydroxy-5-[3-(1H-indol-5-yloxy)-1-methyl-(1E)-propenyl]-tetrahydro-furan-2-yloxy}-3-hydroxy-phenyl)-2-methyl-N- ((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-3,4-Dihydroxy-5-[3-(1H-indol-5-yloxy)-1-methyl-(1Z)-propenyl]-tetrahydro-furan-2-yloxy}-3-hydroxy-phenyl)-2-methyl-N- ((3aS,4R,5R,6S,7R,7aR)-4,6,7-trihydroxy-hexahydro-benzo[1,3]dioxol-5-yl)-(2E)-acrylamide;

3-(4-{(2S,3S,4S,5R)-5-[3-(2-Benzooxazol-2-yl-phenoxy)-1-methyl-(1E)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-acrylamide;

3-(4-{(2S,3S,4S,5R)-5-[3-(2-Benzothiazol-2-yl-phenoxy)-1-methyl-(1Z)-propenyl]-3,4-dihydroxy-tetrahydro-furan-2-yloxy}-3-hydroxy-phenyl)-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-5-(3-Benzenesulfonyl-1-methyl-(1E)-propenyl)-3,4-dihydroxy-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-5-(3-Benzenesulfonyl-1-methyl-(1Z)-propenyl)-3,4-dihydroxy-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-3-phenylsulfanyl-(1E)-propenyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-3-phenylsulfanyl-(1Z)-propenyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-3-phenylamino-(1E)-propenyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-3-phenylamino-(1Z)-propenyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-5-(2-Benzylsulfanyl-1-methyl-(1E)-vinyl)-3,4-dihydroxy-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-5-(2-Benzylsulfanyl-1-methyl-(1Z)-vinyl)-3,4-dihydroxy-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-2-phenylmethanesulfonyl-(1E)-vinyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-2-phenylmethanesulfonyl-(1Z)-vinyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-2-phenylsulfamoyl-(1E)-vinyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-3,4-Dihydroxy-5-(1-methyl-2-phenylsulfamoyl-(1Z)-vinyl)-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-5-(2-Fluoro-1-methyl-3-phenoxy-(1E)-propenyl)-3,4-dihydroxy-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

3-{4-[(2S,3S,4S,5R)-5-(2-Fluoro-1-methyl-3-phenoxy-(1Z)-propenyl)-3,4-dihydroxy-tetrahydro-furan-2-yloxy]-3-hydroxy-phenyl}-2-methyl-N-((3aS,4R,5R,6S,7R,7aR)-4,6,7-trihydroxy-hexahydro-benzo[1,3]dioxol-5-yl)-(2E)-acrylamide;

and the pharmaceutically acceptable salts and solvates of said compounds.

13. A pharmaceutical composition for the treatment of a bacterial infection, a protozoal infection, or a disorder caused by a bacterial infection or a protozoal infection, in a mammal, fish, or bird which comprises a therapeutically effective amount of a compound of claim 1 and a pharmaceutically acceptable carrier.

14. A method of treating a bacterial infection, a protozoal infection, or a disorder caused by a bacterial infection or a protozoal infection, in a mammal, fish, or bird which comprises administering to said mammal, fish or bird a therapeutically effective amount of a compound of claim 1.

15. A method of preparing a compound of the formula

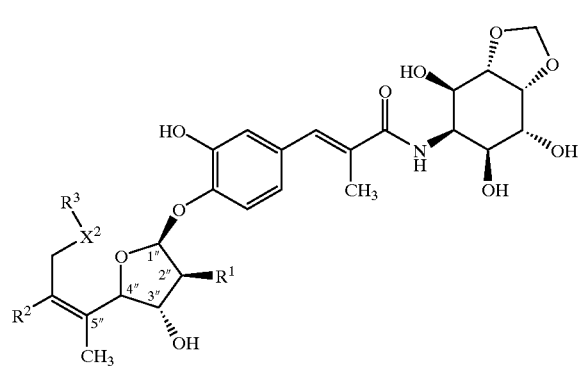

3 or a pharmaceutically acceptable salt or solvate thereof wherein:

$X^2$ is O or S;

$R^1$ is H or OH;

$R^2$ is H, $C_1$–$C_6$ alkyl, or halo, wherein the foregoing $R^2$ alkyl group is optionally substituted by 1 or 2 $R^4$ groups;

$R^3$ is —$(CR^6R^7)_t(C_6$–$C_{10}$ aryl) wherein t is an integer from 0 to 5 and the aryl moiety of the foregoing $R^3$ group is optionally substituted by 1 to 5 $R^4$ groups;

each R[4] is independently selected from the group consisting of $C_1$–$C_{10}$ alkyl, $C_2$–$C_{10}$ alkenyl, $C_2$–$C_{10}$ alkynyl, halo, cyano, nitro, trifluoromethyl, trifluoromethoxy, azido, hydroxy, $C_1$–$C_6$ alkoxy, —C(O)R[5], —C(O)OR[5], —NR[6]C(O)OR[8], —OC(O)R[5], —NR[6]SO$_2$R[8], —SO$_2$NR[5]R[6], —NR[6]C(O)R[5], —C(O)NR[5]R[6], —NR[5]R[6], —S(O)$_j$(CR[6]R[7])$_m$($C_6$–$C_{10}$ aryl), —S(O)$_j$($C_1$–$C_6$ alkyl), —(CR[6]R[7])$_m$($C_6$–$C_{10}$ aryl), —O(CR[6]R[7])$_m$($C_6$–$C_{10}$ aryl), —NR[6](CR[6]R[7])$_m$($C_6$–$C_{10}$ aryl), —(CR[6]R[7])$_m$(4–10 membered heterocyclic), —C(O)(CR[6]R[7])$_m$($C_6$–$C_{10}$ aryl), and —C(O)(CR[6]R[7])$_m$(4–10 membered heterocyclic), wherein m is an integer from 0 to 4; j is an integer from 0 to 2, and said alkyl, alkenyl, alkynyl, aryl and heterocyclic moieties of the foregoing R[4] groups are optionally substituted by 1 to 3 substituents independently selected from the group consisting of halo, cyano, nitro, trifluoromethyl, trifluoromethoxy, azido, —NR[6]SO$_2$R[8], —SO$_2$NR[5]R[6], —C(O)R[5], —C(O)OR[5], —OC(O)R[5], —NR[6]C(O)OR[8], —NR[6]C(O)R[5], —C(O)NR[5]R[6], —NR[5]R[6], —OR[5], $C_1$–$C_{10}$ alkyl, —(CR[6]R[7])$_m$($C_6$–$C_{10}$ aryl), and —(CR[6]R[7])$_m$(4–10 membered heterocyclic), wherein m is an integer from 0 to 4;

each R[5] is independently selected from the group consisting of H, $C_1$–$C_{10}$ alkyl, —(CR[6]R[7])$_m$($C_6$–$C_{10}$ aryl), and —(CR[6]R[7])$_m$(4–10 membered heterocyclic), wherein m is an integer from 0 to 4, and the foregoing R[5] substituents, except H, are optionally substituted by 1 to 3 substituents independently selected from the group consisting of halo, cyano, nitro, trifluoromethyl, trifluoromethoxy, azido, —C(O)R[6], —C(O)OR[6], —OC(O)R[6], —NR[6]C(O)R[7], —C(O)NR[6]R[7], —NR[6]R[7], hydroxy, $C_1$–$C_6$ alkyl, and $C_1$–$C_6$ alkoxy;

each R[6] and R[7] is independently H, —C(O)($C_1$–$C_6$ alkyl), $C_1$–$C_6$ alkyl or fluoro; and, R[8] is selected from the substituents provided in the definition of R[5] except R[8] is not H;

which comprises treating a compound of the formula

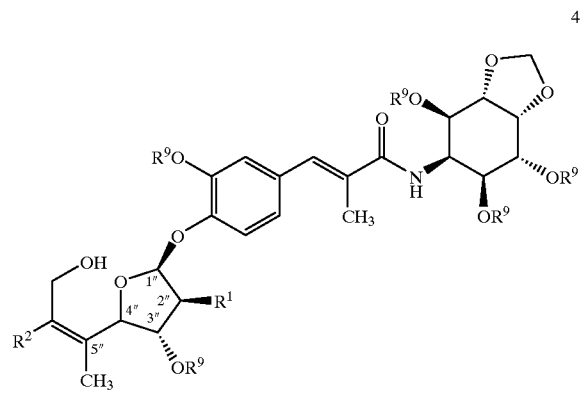

4 wherein R[1] and R[2] are as defined above, provided that if R[1] is hydroxy it is protected as —OR[9], and R[9] is a hydroxy protecting group, with a compound of the formula H—X[2]—(CR[6]R[7])$_t$($C_6$–$C_{10}$ aryl), wherein t is 0 and X[2], R[6], and R[7] are as defined above, in the presence of triphenylphosphine and diethylazodicarboxylate, followed by deprotection of the R[9]-protected hydroxy groups.

16. The method of claim 15 wherein R[9] is a silyl group.

* * * * *